United States Patent [19]

Bair

[11] Patent Number: 4,803,221
[45] Date of Patent: Feb. 7, 1989

[54] ANTHRACENE DERIVATIVES

[75] Inventor: Kenneth W. Bair, Chapel Hill, N.C.

[73] Assignee: Burroughs Wellcome Co., Research Triangle Park, N.C.

[21] Appl. No.: 90,569

[22] Filed: Aug. 28, 1987

Related U.S. Application Data

[60] Division of Ser. No. 661,802, Oct. 17, 1984, Pat. No. 4,719,099, which is a continuation-in-part of Ser. No. 499,332, May 31, 1983, abandoned.

[51] Int. Cl.[4] ................. C07C 93/00; C07C 87/78; C07C 87/64
[52] U.S. Cl. ................... 514/510; 260/501.1; 260/501.12; 260/501.18; 260/501.21; 560/5; 560/257; 564/341; 564/366; 564/387; 564/391; 564/426; 564/427; 564/440; 564/442; 564/443; 558/413; 558/414; 558/422; 514/577; 514/653; 514/908
[58] Field of Search ........... 260/501.18, 501.1, 501.12, 260/501.21; 564/387, 341, 366, 391; 514/510, 577, 653, 908; 560/5, 257; 558/413, 414, 422

[56] References Cited

U.S. PATENT DOCUMENTS

| | | | |
|---|---|---|---|
| 2,530,065 | 11/1950 | King | 560/39 |
| 2,574,150 | 11/1951 | Kerwin et al. | 260/501.18 |
| 3,198,802 | 8/1965 | Clark et al. | 560/38 |
| 4,511,582 | 4/1985 | Bair | 514/654 |
| 4,530,800 | 7/1985 | Bair | 260/501.21 |
| 4,532,344 | 7/1985 | Bair | 560/252 |
| 4,551,282 | 11/1985 | Bair | 260/501.18 |
| 4,719,046 | 1/1988 | Bair | 260/501.18 |
| 4,719,047 | 1/1988 | Bair | 260/501.18 |
| 4,719,048 | 1/1988 | Bair | 260/501.18 |
| 4,719,049 | 1/1988 | Bair | 260/501.18 |
| 4,719,055 | 1/1988 | Bair | 260/501.18 |
| 4,720,587 | 1/1988 | Bair | 564/387 |

FOREIGN PATENT DOCUMENTS 743137  9/1966  Canada .................... 564/426

OTHER PUBLICATIONS

Investigational New Drugs 2, 1984, Bradley et al. pp. 59–70 "The Bender Tumor Colony-Forming Chemosensitivity Assay."
Dow Jones New Wire, 4/22/88 #160425-0097.
Hrabowska, M., et al., "Antitumo Activity of 1-Nitro-9 amino aeridix Perserative", Angneiun-Forsch/Drug No. 32(11), No. 9 (1982), 1013–1016.

Primary Examiner—Glennon H. Hollrah
Assistant Examiner—Raymond Covington
Attorney, Agent, or Firm—Donald Brown

[57] ABSTRACT

The present invention relates to compounds of formula (I)

$$ArCH_2R^1 \qquad (I)$$

or a monomethyl or a monoethyl ether thereof (the compound of formula (I) including these ethers may contain no more than 30 carbon atoms in total); ethers, esters thereof; acid addition salts thereof; wherein Ar is an anthracene or substituted anthracene ring system; $R^1$ contains not more than eight carbon atoms and is a group

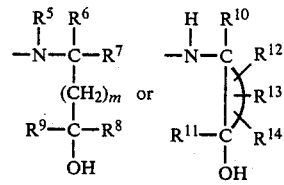

wherein
  m is 0 or 1;
  $R^5$ is hydrogen;
  $R^6$ and $R^7$ are the same or different and each is hydrogen or $C_{1-3}$ alkyl optionally substituted by hydroxy;
  $R^8$ and $R^9$ are the same or different and each is hydrogen or $C_{1-3}$ alkyl;

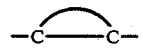

is a five- or six-membered saturated carbocyclic ring;
  $R^{10}$ is hydrogen, methyl or hydroxymethyl;
  $R^{11}$, $R^{12}$ and $R^{13}$ are the same or different and each is hydrogen or methyl;
  $R^{14}$ is hydrogen, methyl, hydroxy, or hydroxymethyl.

11 Claims, No Drawings

ANTHRACENE DERIVATIVES

This is a divisional of co-pending application Ser. No. 661,802 filed on Oct. 17, 1984, now U.S. Pat. No. 4,714,099, which is a continuation in part of Ser. No. 499,332, filed May 31, 1983, now abandoned.

The present invention relates to polycyclic aromatic alkanol derivatives which have been found to have biocidal activity. More specifically the invention concerns aminoalkanol derivatives containing a polycarbocyclic aromatic ring system, methods for the synthesis thereof, pharmaceutical formulations thereof, novel intermediates therefor, pharmaceutical formulations thereof and the use thereof as biocidal agents, particularly antitumor agents.

Accordingly, in a first aspect, the present invention provides a compound of the formula (I):

$$ArCH_2R^1 \quad (I)$$

or a monomethyl or monoethyl ether thereof (the compound of formula (I) including these ethers may contain no more than 30 carbon atoms in total); ethers, esters thereof; acid addition salts thereof; wherein Ar is an anthracene ring optionally substituted by one, two, or three substituents (the substituents will contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the anthracene ring is optionally substituted by a group $NR^3R^4$ containing not more than 5 carbon atoms wherein $R^3$ and $R^4$ are the same or different and each is a $C_{1-3}$ alkyl group or $NR^3R^4$ forms a five- or six-membered heterocyclic ring optionally containing one or two additional heteroatoms);

$R^1$ contains not more than eight carbon atoms and is a group

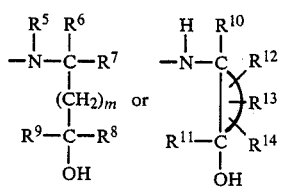

wherein
m is 0 or 1;
$R^5$ is hydrogen;
$R^6$ and $R^7$ are the same or different and each is hydrogen or $C_{1-3}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;

$R^{14}$ is hydrogen, methyl, hydroxy, or hydroxymethyl.

Suitably $ArCH_2R^1$ or a monomethyl or monethyl ether thereof contains not more than 28 carbon atoms in total.

Ar is suitably 1- or 9-anthracenyl,

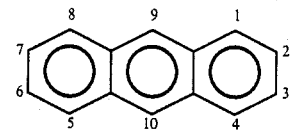

suitably m is 0, suitably $R^1$ is

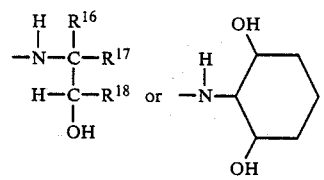

wherein
$R^{16}$ is $CH_2OH$, $CH(CH_3)OH$ or $CH_2CH_2OH$,
$R^{17}$ is hydrogen, $C_{1-3}$ alkyl or $CH_2OH$,
$R^{18}$ is hydrogen or methyl.
Preferably $R^{16}$ is $CH_2OH$ or $CH(CH_3)OH$; $R^{17}$ is hydrogen, methyl, ethyl or $CH_2OH$; Ar is 9-anthracenyl.

Most preferably $R^1$ is a diol of structure

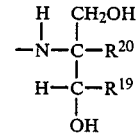

wherein
$R^{19}$ is hydrogen or methyl and
$R^{20}$ is hydrogen, methyl or ethyl, preferably methyl.

Acid addition salts included within the scope of the present invention are those of compound of formula (I) and ethers and esters thereof.

Esters and nonpharmaceutically useful acid addition salts of the compounds of the formula (I) are useful intermediates in the preparation and purification of compounds of the formula (I) and pharmaceutically useful acid addition salts thereof, and are therefore within the scope of the present invention. Thus, acid addition salts of the compounds of the formula (I) useful in the present invention include but are not limited to those derived from inorganic acids, such as hydrochloric, hydrobromic, sulfuric and phosphoric acids, and organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids, and amino acids such as glycine. Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, lactic, citric and isethionic acids.

The preferred pharmacologically and pharmaceutically acceptable salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from $C_{1-6}$ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include:

2-(((10-Chloro-9-anthracenyl)methyl)amino)-2-methyl-1,3-propanediol,
2-((9-Anthracenylmethyl)amino)-2-methyl-1,3-propanediol,
2-Methyl-2-(((10-methylthio-9-anthracenyl)methyl)amino)-1,3-propanediol,
2-(((10-(2-Chloroethyl)-9-anthracenyl)methyl)amino)-2-methyl-1,3-propanediol,
2-(((4,10-Dichloro-9-anthracenyl)methyl)amino)-2-methyl-1,3-propanediol,
2-(((10-Hydroxymethyl-9-anthracenyl)methyl)amino)-2-methyl-1,3-propanediol,
2-Methyl-2-(((10-methyl-9-anthracenyl)methyl)amino)-1,3-propanediol,
2-(((10-Bromo-9-anthracenyl)methyl)amino)-2-methyl-1,3-propanediol,
2-(((10-Chloro-9-anthracenyl)methyl)amino)-2-ethyl-1,3-propanediol,
2-(((4,5-Dichloro-9-anthracenyl)methyl)amino)-2-methyl-1,3-propanediol,
2-(((4-Chloro-9-anthracenyl)methyl)amino)-2-methyl-1,3-propanediol,
2-Methyl-2-(((10-methylsulfinyl-9-anthracenyl)methyl)amino)-1,3-propanediol,
2-(((10-Methoxy-9-anthracenyl)methyl)amino)-2-methyl-1,3-propanediol,
10-((1,1-Bis(hydroxymethyl)ethylamino)methyl)-9-anthracenecarbonitrile,
2-(((10-Bromo-1-anthracenyl)methyl)amino)-2-methyl-1,3-propanediol,
2-((1-Anthracenylmethyl)amino)-2-methyl-1,3-propanediol,
2-(((2-Chloro-9-anthracenyl)methyl)amino)-2-methyl-1,3-propanediol,
2-(((10-Ethylthio-9-anthracenyl)methyl)amino)-2-methyl-1,3-propanediol,
2-(((10-(2-Hydroxyethylthio)-9-anthracenyl)methyl)amino)-2-methyl-1,3-propanediol,
2-(((10-Chloro-9-anthracenyl)methyl)amino)-2-hydroxymethyl-1,3-propanediol,
2-(((3,10-Dichloro-9-anthracenyl)methyl)amino)-2-methyl-1,3-propanediol,
2-(((2,10-Dichloro-9-anthracenyl)methyl)amino)-2-methyl-1,3-propanediol,
2-(((10-Ethoxy-9-anthracenyl)methyl)amino)-2-methyl-1,3-propanediol,
2-(((10-(2-Hydroxyethoxy)-9-anthracenyl)methyl)amino)-2-methyl-1,3-propanediol,
2-Methyl-2-(((10-methylsulfonyl-9-anthracenyl)methyl)amino)-1,3-propanediol,
2-(((3-Chloro-9-anthracenyl)methyl)amino)-2-methyl-1,3-propanediol,
2-(((2-Ethyl-9-anthracenyl)methyl)amino)-2-methyl-1,3-propanediol and 2-(((3-Ethyl-9-anthracenyl)methyl)amino)-2-methyl-1,3-propanediol,
(+ —)(2R*,3S*)-2-((9-Anthracenylmethyl)amino)-2-methyl-1,3-butanediol,
2-((9-Anthracenylmethyl)amino)-2-ethoxymethyl-1,3-propanediol,
2-(((10-chloro-1-anthracenyl)methyl)amino-2-methyl-1,3-propanediol,
2-(((10-(2-Methoxyethoxy)-9-anthracenyl)methyl)amino)-2-methyl-1,3-propanediol,
2-Methyl-2-(((10-N-morpholino-9-anthracenyl)methyl)amino)-1,3-propanediol,
2-((9-Anthracenylmethyl)amino)-3-methoxy-2-methyl-1-propanol,
2-((9-Anthracenylmethyl)amino)-2-isopropyl-1,3-propanediol,
2-((9-Anthracenylmethyl)amino)-2-methyl-1,4-butanediol,
2-(((10-(1H-Imidazol-1-yl)-9-anthracenyl)methyl)amino)-2-methyl-1,3-propanediol,
(1α,2β,3α)-2-((9-Anthracenylmethyl)amino)-1,3-cyclohexanediol,
2-(((4-Chloro-10-(2-hydroxyethoxy)-9-anthracenyl)methyl)amino)-2-methyl-1,3-propanediol,
2-Methyl-2-(((4,5,10-trichloro-9-anthracenyl)methyl)amino)-1,3-propanediol,
2-(((10-Chloro-2,3-dimethyl-9-anthracenyl)methyl)amino)-2-methyl-1,3-propanediol,
2-(((2-tert-Butyl-10-chloro-9-anthracenyl)methyl)amino)-2-methyl-1,3-propanediol,
2-(((3-tert-Butyl-10-chloro-9-anthracenyl)methyl)amino)-2-methyl-1,3-propanediol,
2-((2-Anthracenylmethyl)amino)-2-methyl-1,3-propanediol,
2-Methyl-2-((2,6,10-trichloro-9-anthracenyl)methyl)amino)1,3-propanediol,
2-(((10-Butoxy-9-anthracenyl)methyl)amino)-2-methyl-1,3-propanediol and
2-(((10-Butyl-9-anthracenyl)methyl)amino)-2-methyl-1,3-propanediol;
ethers, esters thereof; acid addition salts thereof.

Of these specific examples of compounds of formula (I), the most preferred compound is 2-((10-(2-hydroxyethoxy)-9-(anthracenylmethyl)amino)-2-methyl-1,3-propanediol; ethers, esters thereof; acid addition salts thereof.

The compounds of formula (I) and their ethers, esters and salts thereof may be prepared by any method known in the art for the preparation of compounds of analogous structure. Thus, the compounds of formula (I) may, for example, be prepared by any of the methods defined below.

1. The reduction of a compound of formula (II)

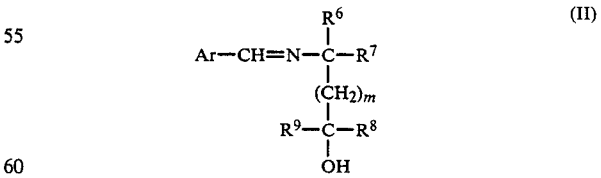

wherein $R^1$–$R^4$ are as hereinbefore defined or an appropriately protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction is conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagents as outlined catalyst such as palladium or platinum, or equivalent reagents as outlined by J. March, *Advanced Organic Chemistry*, 2nd ed., pages 819-820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethylether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et al., *Organic Preparations and Procedures International* 11, 201 (1979).

In the case of catalytic hydrogenation, suitable solvents include alcohols (for example methanol and ethanol) optionally in the presence of a hydrocarbon cosolvent (for example toluene or benzene) or ether cosolvent (for example diethyl ether or tetrahydrofuran) in the presence of an acid (for example glacial acetic acid or ethanolic hydrochloric acid) or in glacial acetic acid.

Protected derivatives of compounds of formula (II) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

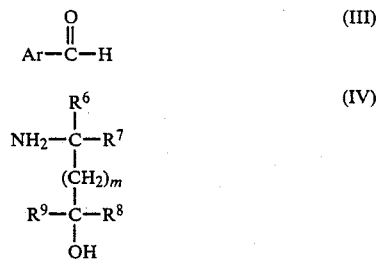

wherein Ar and $R^1$-$R^4$ are as defined in (I), and reduce the compound of the formula (II) so formed in situ. The reaction of the compounds of the formulae (III) and (IV) is again suitable carried out using conditions and reagents which are well known to those skilled in the art, for example in the presence of an acid, such as a sulfonic acid, i.e. p-toluenesulfonic acid, in an appropriate inert solvent, such as an aromatic hydrocarbon, suitable toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cyanoborohydride.

The compound of formula (III) may be in the form of a protected aldehyde, for example an acetal, which liberates the aldehyde function under the reaction conditions.

In turn, a compound of formula (III) can be synthesized by reacting the appropriate polycyclic aromatic hydrocarbon with a formylating agent such as that generated by the reaction between $SnCl_4$ and $Cl_2CHOCH_3$ or equivalent reagents, for example, according to the method of A. Reiche et al., *Chem. Ber.* 93, 88 (1960), or with other standard formylating reagents/procedures known to the art, for example, the Gatterman-Koch reaction ($CO/HCl/AlCl_3/CuCl$), the Gatterman reaction ($HCN/HCl/ZnCl_2$), and the Vilsmeier reaction ($POCl_3/PhN(Me)CHO$, or $POCl_3/Me_2NCHO$) (J. March, vide supra, pages 494-497).

The compounds of the formula (III) may also be prepared from an appropriate polycyclic aromatic hydrocarbon substituted by a suitable functional group such as $CH_2OH$, $CHBr_2$, $CH_3$, $COCH_3$, $COOH$, or $CN$, and converting this functional group to an aldehyde group by methods well known to those skilled in the art.

Where the polycyclic aromatic ring bears *substituents*, the compound of formula (III) may be prepared by a variety of methods known in the art of organic chemistry depending on the nature of the substituent on the polycyclic ring. For example, if the substituent(s) is a halogen, the starting materials may be prepared by direct treatment of the polycyclic aromatic hydrocarbon with a halogenating agent (e.g. $Cl_2$, $Br_2$, or $SO_2Cl_2$) or indirectly by such routes as the Sandmeyer reaction (H. H. Hodgson, *Chem. Rev.* 40, 251 (1947). If the substituent(s) is alkyl, the polycyclic aromatic hydrocarbon may be reacted with the appropriate reagents under Friedel-Crafts reaction conditions (G. A. Olah, *Friedel Crafts and Related Reactions*, Vols. 1-3, Interscience, New York, NY, 1963-1965).

The compounds of the formula (IV) also may be prepared by methods known in the art, for example, by the reaction of compound $NO_2CH_2R^2$ with an appropriate aldehyde, conveniently acetaldehyde or formaldehyde (as in B. M. Vanderbilt and H. B. Hass, *Ind. Eng. Chem.* 32, 34 (1940)) followed by reduction (as outlined in J. March, vide supra, pages 1125-1126), conveniently by hydrogen and a metal catalyst (for example, a platinum containing catalyst) in an appropriate solvent, conveniently glacial acetic acid.

2. The reduction of a compound of the formula (V)

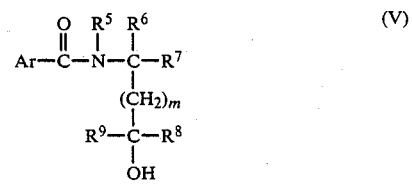

wherein Ar and $R^1-R^4$ are as hereinbefore defined and the hydroxy groups are optionally protected, followed by deprotection of the hydroxy groups where appropriate. The reduction may be carried out by standard reducing agents appropriate. The reduction may be carried out by standard reducing agents known for carrying out this type of reduction (as outlined in J. March, vide supra page 1122), for example, a hydride reagent such as lithium aluminium hydride in an inert solvent, such as an ether, i.e. tetrahydrofuran, at a non-extreme temperature, for example, at between 0° and 100° C. and conveniently at the reflux temperature of the ether.

The compound of the formula (V) may be formed by the reaction of the appropirate acid (ArCOOH) or a suitable reactive acid derivative thereof (as outlined in J. March, vide supra, pages 382–390), for example, an acid halide, in an inert solvent with an amine of the formula (IV) in which the hydroxy groups are optionally protected, for example, when the compound of the formula (IV) is a diol, by an isopropylidene group. The compound of the formula (V) so formed is suitably reduced in situ and deprotected if necessary to give a compound of formula (I). The compounds of the formula ArCOOH can be prepared by methods well known to those skilled in the art.

3. The reaction of a compound $ArCH_2L$ (wherein Ar is as hereinbefore defined and L is a leaving group) with a compound of the formula (IV) as hereinbefore defined. Suitable leaving groups are those defined by J. March, vide supra, pages 325–331, and include halogens such as chlorine and bromine and sulfonic acid derivatives such as p-toluenesulfonate. The reaction is suitably carried out in an appropriate solvent, such as a dipolar aprotic solvent or alcohol at a non-extreme temperature, for example 50°–100°. The compounds of the formula $ArCH_2L$ can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g. are toxic to certain living cells which are detrimental to mammals, for example pathogenic organisms and tumor cells.

This toxicity to pathogenic organisms has been demonstrated by activity against viruses (e.g. *Herpes simplex* 1/vero), fungi (e.g. *Candida albicans*), protozoa (e.g. *Eimeria tenella* and *Trichomonas vaginalis*), bacteria (e.g., *Mycoplasma smegmatis* and *Streptococcus pyogenes*), and helminths (e.g. *Nippostrongylus brasiliensis*). The antitumor activity of compounds of formula (I) has been demonstrated in a number of recognized screens and primarily by activity against ascitic P388/0 leukemia. Preferred compounds of the formula (I) are those which have antitumor activity. The activity against ascitic tumors, including P388/0, is evidenced by reduction of tumor cell number in mammals (for example, mice bearing ascitic tumors) and their consequent increase in survival duration as compared to an untreated tumor bearing control group. Antitumor activity is further evidenced by measurable reduction in the size of solid tumors following treatment of mammals with the compounds of this invention compared to the tumors of untreated control tumor bearing animals. Compounds of formula (I) are active against murine tumors such as lymphocytic leukemia P388/0, lymphocytic leukemia L1210, malanotic melanoma B16, P815 mastocytoma, MDAY/D2 fibrosarcoma, colon 38 adenocarcinoma, M5076 rhabdomyosarcoma and Lewis lung carcinoma. Activity in one or more of these tumor tests has been reported to be indicative of antitumor activity in man (A. Goldin et al. in *Methods in Cancer Research* ed. V. T. DeVita Jr. and H. Busch, 16 165, Academic Press, N.Y. 1979).

There are sublines of P388/0 which have made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/0 above.

Compounds of formula (I) have also been found to be active against human tumor cells in primary cultures of lung, ovary, breast, renal, melanoma, unknown primary, gastric, pancreatic, mesothelioma, myeloma, and colon cancer. (As used herein "cancer" is to be taken as synonymous with "malignant tumor" or more generally "tumor" unless otherwise noted.) This is a procedure in which the prevention of tumor cell colony formation, i.e. tumor cell replication, by a drug has been shown to correlate with clinical antitumor activity in man (D. D. Von Hoff et al., *Cancer Chemotherapy* and *Pharmacology* 6, 265 (1980); S. Salmon and D. D. Von Hoff, *Seminars in Oncology*, 8, 377 (1981)).

Compounds of formula (I) which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between $-2.0$ and $+2.5$.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a biocidal agent will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day, or by intravenous infusion for a selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula I given 4 times per day in a pharmaceutically useful formulation.

While it is possible for the active compound (defined herein as compound of formula (I), or ether, ester, or salt thereof) to be administered alone, it is preferable to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefore.

There is also provided a method for the preparation of a pharmaceutical formulation comprising bringing into association a compound of formula (I), an ether, ester, or pharmaceutically acceptable salt thereof, and a pharmaceutically acceptable carrier therefore.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

GENERAL COMMENTS

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A macine using two 500 g silica gel ($SiO_2$) cartridges unless otherwise noted. Plugs of $SiO_2$ used for purification were "flash chromatography" $SiO_2$ (Merck & Co., Inc., Merck Chemical Division, Rahway, N.J., 07065, silica gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of ≦0.4% of the expected value). Any changes to the procedure such as solvent, reaction temperature, reaction time, or workup are noted.

NMR ($^1H$, $^{13}C$), IR, MS data of all new products were consistent with the expected and proposed structures.

The positions assigned to structural isomers were unequivocally determined by a number of NMR techniques. All final products were dried in a vacuum oven at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

EXAMPLE 1

2-((9-Anthracenylmethyl)amino)-2-methyl-1,3-propanediol hydrochloride

To a 2 L Erlenmeyer flask was added 9-anthracenecarbaldehyde (Aldrich Chemical Co., Milwaukee, WI, 53201, 20.63 g, 0.1 mol) 2-methyl-2-amino-1,3-propanediol (Aldrich, 9.13 g, 86.8 mmol), p-toluenesulfonic acid.$H_2O$ (Eastman Kodak Co., Rochester, NY, 14650, 0.1 g, 0.5 mmol), and $PhCH_3$ (500 mL). The mixture was warmed to reflux for a few minutes and $H_2O$ (2–3 mL) was driven off. The resulting golden colored solution was allowed to cool to RT, diluted with abs. EtOH (500 mL) and stirred overnight. $NaBH_3CN$ (Aldrich, 95%, 2.51 g, 42 mmol) was added to the reaction. After the $NaBH_3CN$ dissolved, an indicator (bromocresol green, Eastman, 5 mg) was added. To the resulting blue solution was added 5 drops of 1M solution of HCl gas in abs. EtOH every 15 minutes. After 3 days the indicator turned green then yellow and voluminous white precipitate was present in the flask. To the flask was then added 1M HCl gas (10 mL) in abs. EtOH. The reaction was diluted to 4 L with $Et_2O$ and stirred for 1 h. The precipitate was then collected by filtration through a medium porosity glass fritted funnel and pressed dry. The filter cake was washed with $CH_2Cl_2$ (4×500 mL), pressed and sucked dry, and dried (100°). The crude solid was recrystallized from EtOH/$Et_2O$ (3×) to give 13.44 g (40%) of 2-((9-anthracenylmethyl)amino)-2-methyl-1,3-propanediol hydrochloride mp 139°–140° (dec), (C, H, Cl, N).

EXAMPLE 2

2-(((10-Chloro-9-anthracenyl)methyl)amino)-2-methyl-1,3-propanediol

2A.

2-(((10-Chloro-9-anthracenyl)methyl)amino-2-methyl-1,3-propanediol hydrochloride Using the reductive amination procedure outlined in 1, 10-chloroanthracene-9-carbaldehyde (Aldrich) and 2-amino-2-methyl-1,3-propanediol (Aldrich) gave 2-(((10-chloro-9-anthracenyl)methyl)amino)-2-methyl-1,3-propanediol hydrochloride mp 268°–269° (dec), ($CH_3OH/Et_2O$), (C, H, Cl, N).

2B.

2-(((10-Chloro9-anthracenyl)methyl)amino-2-methyl-1,3-propanediol methanesulfonate To a RB flask equipped with magnetic stirring bar, condenser, Dean-Stark trap and $N_2$ bubbler was added 10-chloroanthracene-9-carbaldehyde (Aldrich, 50.0 g, 0.208 mol, 2-amino-2-methyl-1,3-propanediol (Aldrich, 43.7 g, 0.415 mol) p-toluenesulfonic acid monohydrate (Aldrich, 3.98 g, 20.8 mmol) and $PhCH_3$ (750 mL). The mixture was refluxed for 3.5 h with azeotropic removal of $H_2O$. Most of the $PhCH_3$ was then distilled from the mixture. The mixture was then cooled to 0° and diluted with abs. EtOH (700 mL). Solid $NaBH_4$ (MCB Manufacturing Chemists Inc. 2909 Highland Ave., Cincinnati OH, 45212, 9.55 g, 0.252 mol) was then added to the reaction mixture in 0.5 g portions. The reaction was then allowed to warm to RT and stirred overnight. A 1N NaOH solution (10 mL) was then added to the reaction mixture and the solvents removed by rotary evaporation. The solid was then shaken with several portions of 1N NaOH solution (4×300 mL) and filtered. The yellow solid was washed with $H_2O$ (3×500 ml) and sucked semidry. The solid was then dissolved in a mixture of $CH_3OH$ (800 ml) and $CH_3SO_3H$ (Aldrich, 19.3 g, 0.20 mol, 13.0 ml) filtered and diluted to 2.5 L with $Et_2O$. Two further crystallizations gave 2-(((10-chloro-9-anthracenyl)methyl)amino)-2-methyl-1,3-propanediol methanesulfonate mp 234°–235° (dec), ($CH_3OH/Et_2O$), (C, H, Cl, N, S).

Note: In some subsequent procedures the crude free base was treated with a 2M ethanolic HCl solution and then recrystallized in the same fashion as the methanesulfonate salt. Alternatively, the crude reaction mixture could be treated with ethanolic HCl instead of 1N NaOH solution. In these cases after the solvent was removed the solid could be washed with 1N HCl solution filtered and recrystallized. If the HCl salt was too $H_2O$ soluble the material was dissolved in $H_2O$ and filtered through a Celite (trademark) pad, basified, filtered and treated as above.

EXAMPLE 3

2-Methyl-2-(((10-methylthio-9-anthracenyl)methyl)amino)-1,3-propanediol

3A. 10-Methylthio-9-anthracenecarbaldehyde

The procedure of V. Rogovik et al., *Zh. Org. Khim.* 3 1315 (1969) was modified in the following way: A 2 L 3-neck flask fitted with stirring bar, condenser, addition funnel, thermometer, $N_2$ inlet and bubbler was charged with 10-chloro-9-anthracenecarbaldehyde (Aldrich, 28.0 g, 0.116 mol) and DMF (Aldrich, 1 L). The solid dissolved when the reaction mixture was warmed to 60°. The addition funnel was filled with a solution of $Na_2S$ (Mallinckrodt, 28 g, 0.116 mol) in 30 mL of $H_2O$. This solution was added rapidly to the flask causing a considerable amount of spattering as the purple thiolate formed. The reaction mixture was stirred at 65° for 45 min, then cooled to 30° (ice bath). $CH_3I$ (Aldrich, 27.36 g, 0.193 mol) was then added to the flask dropwise over 5 min. The color of the solution changed from deep purple to yellow after 3 h. After an additional 15 min, 1 L of $H_2O$ was added to the reaction mixture. The yellow solid that formed was collected by filtration, dissolved in hot $PhCH_3$, (500 ml) dried ($MgSO_4$), and chromatographed on a plug of $SiO_2$. Most of the volume of $PhCH_3$ was removed and the resultant oil was swirled with hexane (200 mL) to give a bright yellow solid. The material was dried at 50°, affording 25.04 g (86%) of 10-methylthio-9-anthracenecarbaldehyde mp 98.5°–99°, (C, H, S).

3B.

2-Methyl-2-(((10-methylthio-9-anthracenyl)methyl)amino)-1,3-propanediol hydrochloride Using the reductive animation procedure outlined in 1,10-methylthioanthracene-9-carbaldehyde (3A) and 2-amino-2-methyl-1,3-propanediol (Aldrich) gave 2-methyl-2-(((10-methylthio-9-anthracenyl)methyl)amino)-1,3-propanediol hydrochloride mp 225°–226° (dec), (EtOH/$Et_2O$), (C, H, Cl, N, S).

3C.
2-Methyl-2-(((10-methylthio-9-anthracenyl)methyl)amino)-1,3-propanediol methanesulfonate Using the reductive animation procedure outlined in 2B, the two intermediates in 3B gave 2-methyl-2-(((10-methyl-9-anthracenyl)methyl)amino)-1,3-propanediol methanesulfonate mp 193°-194°, (EtOH/Et$_2$O), (C, H, N, S).

EXAMPLE 4
2-(((10-(2-Chloroethyl)-9-anthracenyl)methyl)amino)-2-methyl-1,3-propanediol

4A. 10-(2-Chloroethyl)-9-anthracenecarbaldehyde

Using the Vilsmeier procedure (L. F. Fieser et al., *Org. Syn. Coll. Vol. III*, 98 (1955)), 9-vinylanthracene (Aldrich) gave 10-(2-chloroethyl)-9-anthracenecarbaldehyde mp 158°-159°, (PhCH$_3$/CH$_3$OH), (C, H, Cl).

4B.
2-(((10-(2-chloroethyl)-9-anthracenyl)methyl)amino)-2-methyl-1,3-propanediol hydrochloride Using the reductive amination procedure outlined in 1,10-(2-chloroethyl)-9-anthracenecarbaldehyde (4A) and 2-amino-2-methyl-1,3-propanediol (Aldrich) gave 2-(((10-(2-chloroethyl)-9-anthracenyl)methyl)amino)-2-methyl-1,3-propanediol hydrochloride mp 229°-231° (dec), (EtOH/Et$_2$O), (C, H, Cl, N).

4C.
2-(((10-(2-Chloroethyl)-9-anthracenyl)methyl)amino)-2-methyl-1,3-propanediol methanesulfonate Using the reductive amination procedure outlined in 2B, the two intermediates in 4B gave 2-(((10-(2-chloroethyl)-9-anthracenyl)methyl)amino)-2-methyl-1,3-propanediol methanesulfonate mp 210°-210.5° (dec), (EtOH/Et$_2$O), (C, H, Cl, N, S).

EXAMPLE 5
2-(((4,10-Dichloro-9-anthracenyl)methyl)amino)-2-methyl-1,3-propanediol

5A. 1,10-Dichloro-9-anthracenecarbaldehyde and
5B. 4,10-Dichloro-9-anthracenecarbaldehyde Using the procedure of V. I. Rogovik et al., *Zh. Org. Khim.* 3 1315 (1967), 1-chloroanthraquinone (Aldrich) gave a mixture of 1,10- and 4,10-dichloro-9-anthracenecarbaldehydes. These compounds were separated by preparative HPLC using PhCH$_3$ as the eluting solvent and employing the shave/recycle technique to give 3.05 g (14%) of 1,10-dichloro-9-anthracenecarbaldehyde mp 180.5°-183°, (R$_f$=0.64, SiO$_2$, PhCH$_3$), (C, H, Cl), and 0.59 g (3%) of 4,10-dichloro-9-anthracenecarbaldehyde mp 167°-170°, (R$_f$=0.57, SiO$_2$, PhCH$_3$), (C, H, Cl). Later preparations were more successful when the reaction was run at 95° for the 4 h reaction time rather than increasing the reaction temperature to 125° for the last 2 h period. A second batch of the crude isomeric mixture was used in 66A.

5C.
2-(((4,10-Dichloro-9-anthracenyl)methyl)amino)-2-methyl-1,3-propanediol hydrochloride Using the reductive amination procedure outlined in 1,4,10-dichloro-9-anthracenecarbaldehyde (5B) and 2-amino-2-methyl-1,3-propanediol (Aldrich) gave 2-(((4,10-dichloro-9-anthracenyl)methyl)amino)-2-methyl-1,3-propanediol hydrochloride mp 261°-262° (dec), (EtOH/Et$_2$O), (C, H, Cl, N).

EXAMPLE 6
2-(((10-Hydroxymethyl-9-anthracenyl)methyl)amino)-2-methyl-1,3-propanediol hydrochloride ¼H$_2$O Using the reductive amination procedure outlined in 1,10-hydroxymethyl-9-anthracenecarbaldehyde (made by the method of Y. Lin et al., *J. Org. Chem.* 44 4701 (1979)) and 2-amino-2-methyl-1,3-propanediol (Aldrich) gave 2-(((10-hydroxymethyl-9-anthracenyl)methyl)amino)-2-methyl-1,3-propanediol hydrochloride.¼H$_2$O mp 209°-210° (dec), (EtOH/Et$_2$O), (C, H, Cl, N).

EXAMPLE 7
2-Methyl-2-((10-Methyl-9-anthracenylmethyl)amino)-1,3-propanediol hydrochloride.½H$_2$O Using the reductive amination procedure described in 1,10-methyl-9-anthracenecarbaldehyde (Aldrich) and 2-amino-2-methyl-1,3-propanediol (Aldrich) gave 2-methyl-2-(((10-methyl-9-anthracenyl)methyl)amino)-1,3-propanediol hydrochloride.½H$_2$O mp>300° (dec), (EtOH/Et$_2$O), (C, H, Cl, N).

EXAMPLE 8
2-((10-Bromo-9-anthracenylmethyl)amino)-2-methyl-1,3-propanediol

8A. 10-Bromo-9-anthracenecarbaldehyde

This material was made from 9,10-dibromoanthracene (Eastman, 20 g, 60 mmol) by the procedure of R. Kuhn and H. Fischer, *Chem. Ber.* 94 3060 (1961) with some modifications. In this procedure, the reaction mixture was cooled to −78° before the n-BuLi (Aldrich) was added. The resulting mixture was warmed to RT over 1 h and then refluxed until the crystalline starting material disappeared. The mixture was then cooled to −78° again before the DMF was added (in one portion). The flask was warmed to RT and then quenched with 1M HBr (200 mL). The two-phase system was then extracted with CH$_2$Cl$_2$ (3×500 mL). The extracts were combined, dried (MgSO$_4$), filtered, and the solvent removed to give the crude material. This was purified by preparative HPLC using PhCH$_3$ as the eluting solvent to give 13.06 g (76%) of 10-bromo-9-anthracenecarbaldehyde mp 215°-216.5°, (lit. mp 218°, P. Kuhn and H. Fischer, *Chem. Ber.* 94 3060 (1961)), (C, H, Br).

8B.
2-(((10-Bromo-9-anthracenyl)methyl)amino)-2-methyl-1,3-propanediol hydrochloride Using the reductive amination procedure outlined in 1,10-bromoanthracene-9-carbaldehyde (8A) and 2-amino-2-methyl-1,3-propanediol (Aldrich) gave 2-(((10-bromo-9-anthracenyl)methyl)amino)-2-methyl-1,3-propanediol hydrochloride mp 263°-264° (dec), (CH$_3$OH/Et$_2$O), (C, H, Br, Cl, N).

EXAMPLE 9
2-(((10-Chloro-9-anthracenyl)methyl)amino)-2-ethyl-1,3-propanediol hydrochloride Using the reductive amination outlined in 1,10-chloro-9-anthraldehyde (Aldrich) and 2-amino-2-ethyl-1,3-propanediol (Aldrich) gave 2-(((10-chloro-9-anthracenyl)methyl)amino)-2-ethyl-1,3-propanediol hydrochloride, mp 252°–254° (dec), (CH₃OH/Et₂O), (C, H, Cl, N).

EXAMPLE 10

2-(((4,5-Dichloro-9-anthracenyl)methyl)amino)-2-methyl-1,3-propanediol

10A. 4,5-Dichloro-9-anthracenecarbaldehyde 1,8-Dichloroanthracene, prepared by the method of H. O. House et al. *J. Org. Chem.* 38 1167 (1973), was formylated by the procedure of A. Rieche et al., *Chem. Ber.* 93, 88 (1960) to give 4,5-dichloro-9-anthracenecarbaldehyde mp 218°–220°, (PhCH₃/CH₃OH), (C, H, Cl), (lit. 224°–226°, E. L. Stogryn, *J. Med. Chem.* 17 563 (1974)).

10B. 2-(((4,5-Dichloro-9-anthracenyl)methyl)amino)-2-methyl-1,3-propanediol hydrochloride Using the reductive amination procedure outlined in 1,4,5-dichloro-9-anthracenecarbaldehyde (10A) and 2-amino-2-methyl-1,3-propanediol (Aldrich) gave 2-(((4,5-dichloro-9-anthracenyl)methyl)amino)-2-methyl-1,3-propanediol hydrochloride mp 239.5°–240.5° (dec), (EtOH/Et₂O), (C, H, Cl, N).

10C. 2-(((4,5-Dichloro-9-anthracenyl)methyl)amino)-2-methyl-1,3-propanediol methanesulfonate Using the reductive amination procedure outlined in 2B, the intermediates in 10B gave 2-(((4,5-dichloro-9-anthracenyl)methyl)amino)-2-methyl-1,3-propanediol methanesulfonate mp 252°–253° (dec), (CH₃OH/Et₂O), (C, H, Cl, N, S).

EXAMPLE 11

2-((4-Chloro-9-anthracenylmethyl)amino)-2-methyl-1,3-propanediol

11A. 4-Chloro-9-anthracenecarbaldehyde

1-Chloroanthracene prepared from 1-chloroanthraquinone (Aldrich) by the method of H. O. House et al. (*J. Org. Chem.* 38 1167 (1973)) was formylated by the procedure of A. Rieche et al., *Chem. Ber.* 93, 88 (1960). A mixture of 1- and 4-chloro-9-anthracenecarbaldehydes was obtained which was partially purified by preparative HPLC using PhCH₃ as the eluting solvent. The solid from the purified fraction was then recrystallized 2× from PhCH₃/CH₃OH to give pure 4-chloro-9-anthracenecarbaldehyde mp 129°–131°, (C, H, Cl).

11B. 2-(((4-Chloro-9-anthracenyl)methyl)amino)-2-methyl-1,3-propanediol hydrochloride Using the reductive amination procedure outlined in 1, 4-chloro-9-anthracenecarbaldehyde (11A) and 2-amino-2-methyl-1,3-propanediol (Aldrich) gave 2-(((4-chloro-9-anthracenyl)methyl)amino)-2-methyl-1,3-propanediol hydrochloride, mp 225°–226° (dec), (EtOH/Et₂O), (C, H, Cl, N).

11C. 2-(((4-Chloro-9-anthracenyl)methyl)amino)-2-methyl-1,3-propanediol methanesulfonate Using the reductive amination procedure outlined in 2B, the intermediates in 11B gave 2-(((4-chloro-9-anthracenyl)methyl)amino)-2-methyl-1,3-propanediol methanesulfonate mp 223°–223.5° (dec), (CH₃OH/Et₂O), (C, H, Cl, N, S).

EXAMPLE 12

2-Methyl-2-(((10-methylsulfinyl-9-anthracenyl)methyl)amino)-1,3-propanediol

12A. 10-Methylsulfinyl-9-anthracenecarbaldehyde

A 1 L RB flask fitted with addition funnel and stirring bar was charged with 10-methylthio-9-anthracenecarbaldehyde (example 3A, 12.0 g, 48 mmol) and 450 mL of CH₂Cl₂. The resulting solution was cooled to 5° with an ice bath. A solution of m-chloroperbenzoic acid (MCPBA) (Aldrich (85%), 9.64 g, 48 mmol) in 350 mL of CH₂Cl₂ was then added dropwise to the flask over 1 h. The reaction mixture was allowed to warm to RT over 1 h and then was washed with 5% NaHCO₃ solution (2×500 mL), dried (Na₂SO₄), filtered, concentrated to 500 mL, and passed through a plug of SiO₂ (250 g) using PhCH₃ (5 L) as the eluting solvent. The desired material was then eluted from the SiO₂ using EtOAc (2 L) as solvent. The solvent volume was reduced to 100 mL and then diluted to 700 mL with hexane. The resulting yellow solid was filtered and dried at 50° to give 11.98 g (94%) of 10-methylsulfinyl-9-anthracenecarbaldehyde mp 182°–184°, (C, H, S).

12B. 2-Methyl-2-(((10-methylsulfinyl-9-anthracenyl)methyl)amino)-1,3-propanediol hydrochloride Using the reductive amination procedure outlined in 1, 10-methylsulfinyl-9-anthracenecarbaldehyde (12A) and 2-amino-2-methyl-1,3-propanediol (Aldrich) gave 2-methyl-2-(((10-methylsulfinyl-9-anthracenyl)methyl)amino)-1,3-propanediol hydrochloride mp 266°–268° (dec), (EtOH/Et₂O), (C, H, Cl, N, S).

EXAMPLE 13

2-(((10-Methoxy-9-anthracenyl)methyl)amino)-2-methyl-1,3-propanediol

13A. 10-Methoxy-9-anthracenecarbaldehyde

A 2 L round bottom flask fitted with distilling head, thermometer and condenser was charged with 15-crown-5 (Aldrich, 25.89 g, 0.118 mol), NaOCH₃ (Aldrich, 7.62 g, 0.141 mol), and CH₃OH (50 mL). After 5 min 10-chloro-9-anthracenecarbaldehyde (Aldrich, 28.4 g, 0.118 mol) and 900 mL of dry PhCH₃ were added to the clear colorless solution. The solvent was distilled off until the head temperature reached 108° (300 mL). Additional dry PhCH₃ was added to give a total volume of 1 L. The reaction mixture was refluxed for 4 h, cooled and poured onto a large plug of SiO₂ (1 kg) in a sintered glass funnel. The crude product was chromatographed using PhCH₃ as eluting solvent (5 L). The fractions (250 mL) containing the product were combined (3 L), and the solvent volume reduced to 500 mL. Shiny golden crystals formed and were filtered to give (after drying at 50°) 15.6 g of material. The volume of the filtrate was reduced to 200 mL. More material crystallized and was removed by filtration and dried to give 6.1 g of additional material. The two crops were combined to give 22.51 g (81%) of 10-methoxy-9-anthracenecarbaldehyde, which was used without further purification. Recrystallization gave analytically pure material mp 164.5°–166.5°, (PhCH₃), (C, H), (lit. mp 165°, J. B. Conant and M. Bramann, *J. Amer. Chem. Soc.* 50 2305 (1928)).

13B.
2-(((10-Methoxy-9-anthracenyl)methyl)amino)-2-methyl-1,3-propanediol hydrochloride Using the reductive amination procedure outlined in 1, 10-methoxy-9-anthracenecarbaldehyde (13A) and 2-amino-2-methyl-1,3-propanediol (Aldrich) gave 2-(((10-methoxy-9-anthracenyl)methyl)amino)-2-methyl-1,3-propanediol hydrochoride mp 173°–174° (dec), (EtOH/Et$_2$O), (C, H, Cl, N).

EXAMPLE 14
10-(1,1-Bis(hydroxymethyl)ethylamino)methyl)-9-anthracene carbonitrile

14A. 10-Formyl-9-anthracenecarbonitrile

A 25 mL 2-neck RB flask fitted with thermometer, condenser, N$_2$ inlet, bubbler and stirring bar was charged with 10-chloro-9-anthraldehyde (Aldrich, 5 g, 21 mmol), CuCN (Fisher, 2.14 g, 24 mmol), N-methylpyrrolidinone (Aldrich, 100 mL), dry DMF (Aldrich, 15 mL), and bis(triphenylphosphine) palladium dichloride (Fluka Chemical Corp., 255 Hauser Ave., Hauppauge, NY, 11787, 0.08 g, 0.1 mmol). The mixture was warmed to 170° and stirred 15 h under N$_2$. After 1.5 h, the mixture became homogeneous. The reaction was cooled to 70° and poured into a solution composed of 16 g of FeCl$_3$.6H$_2$O, (Mallinckrodt), 70 mL of 1.0M HCl and 400 mL H$_2$O. The resulting mixture was stirred at 60°–70° for 1 h, filtered and a crude orange solid isolated. This material was dissolved in hot PhCH$_3$ (1 L) and passed through a small plug (100 g) of SiO$_2$. The filtrate was then concentrated to 75 mL and diluted with hexane (200 mL). The orange solid which formed was collected by filtration and dried at 50° to give 3.17 g (68%) of 10-formyl-9-anthracenecarbonitrile mp 270°–275°, (C, H, N).

14B. 10-(1,1-Bis(hydroxymethyl)ethylamino)methyl)-9-anthracenecarbonitrile hydrochloride Using the reductive amination procedure outlined in 1, 10-formyl-9-anthracene-carbonitrile (14A) and 2-amino-2-methyl-1,3-propanediol (Aldrich) gave 10-((1,1-Bis(hydroxymethyl)ethylamino)methyl)-9-anthracenecarbonitrile hydrochloride mp 307°–308°, (CH$_3$OH/Et$_2$O), (C, H, Cl, N).

EXAMPLE 15
2-((1-Anthracenylmethyl)amino)-2-methyl-1,3-propanediol

15A. 9,10-Dihydro-9,10-dioxo-1-anthracenecarboxylic acid

Benzanthrone (Aldrich, technical grade) was purified by chromatography on a plug of SiO$_2$ with PhCH$_3$ as eluent (83% recovery) mp 172°–172.5°, (lit. mp 170°–171°, O. Bally and R. Scholl, Ber. 44 1656 (1911)).

The purified benzanthrone (63.7 g, 0.277 mol) was dissolved in glacial HOAc (1.5 L) (heated to 90°) and stirred with a mechanical stirrer. After cooling to 80°, solid CrO$_3$ (Mallinckrodt, 200 g, 2 mol) was added in 5 g portions over about 4 h. The exothermic reaction maintained the mixture at 80° during this time and CO$_2$ was evolved. After CO$_2$ evolution ceased and the reaction temperature fell, the heating mantle was reapplied and the reaction stirred at 75° for an additional 6 h. The reaction was cooled to RT and stirred overnight. H$_2$O (1.5 L) was then added to the dark-green solution. The reaction was then filtered to give a deep brown solid which was washed with CH$_3$OH (200 mL) until the washings were colorless. The resulting solid was dissolved in hot 2-methoxyethanol (2 L) and filtered through Celite ® to remove a black solid residue. The volume of the solution was reduced to 75 mL (some solid formed) and diluted with CH$_3$OH (100 mL to give the product. This material was removed by filtration to give 32.0 g (46%) of golden brown 9,10-dihydro-9,10-dioxo-1-anthracenecarboxylic acid mp 287°–289°, (C, H), (lit. mp 293°–294°, *Chemistry of Carbon Compounds IIIb*, edited by E. H. Rodd, 1419 (1956), Elsevier, New York).

15B. 1-Anthracenecarboxylic acid

To a 5 L 3-neck flask fitted with condenser, thermometer, and overhead stirrer was added 9,10-dihydro-9,10-dioxo-1-anthracenecarboxylic acid (15A, 90 g, 0.357 mol), Zn dust (Mallinckrodt, 250 g, 3.82 mol), CuSO$_4$.5H$_2$O (Mallinckrodt, 5 g), and 28% NH$_4$OH (Mallinckrodt, 2500 mL). The mixture was heated slowly. A dark-red solution occured as the temperature reched 85°. After 3.5 h, the color of the solution faded to yellow. The reaction was heated an additional 1 H, cooled and the excess Zn removed by filtration. The filter cake was washed with more NH$_4$OH solution (100 mL) and then discarded. The filtrate was carefully acidified to pH 1 with conc. HCl (added in portions over 1 h) affording a light-green precipitate, which was separated by filtration. The solid was washed with H$_2$O (200 mL) and then recrystallized 1× from methoxyethanol/H$_2$O (containing 1% conc. HCl), filtered and dried at 75°, to give 65 g (82%) of 1-anthracenecarboxylic acid mp 249°–250°, (C, H), (lit. mp 245°, *Chemistry of Carbon Compounds IIIb*, edited by E. H. Rodd, 1373 (1956), Elsevier, New York).

15C. (1-Anthracenyl)methanol

To a 500 mL 2-neck flask equipped with condenser, addition funnel with N$_2$ inlet and stirring bar was added 1-anthracenecarboxylic acid (15B, 6.88 g, 31 mmol) and dry THF (250 mL). To the addition funnel, was added a 1M solution of BH$_3$ in THF (Aldrich, 50 mL, 50 mmol) via cannula. The BH$_3$ solution was added over 1 h and the solution stirred overnight at RT. CH$_3$OH was then added until H$_2$ evolution ceased. H$_2$O (5 mL) and then 1N HCl (5 mL) was added to the flask. The solvents were removed and then PhCH$_3$ (100 mL) added to the flask. The PhCH$_3$ was then also removed. The resulting solid was recrystallized from EtOAc/hexane to give 4.3 g (67%) of (1-anthracenyl)-methanol mp 124°–125°, (C, H), (lit. 124°–125°, S. Akiyama et al., *Bull. Chem. Soc. Jap.* 35 (1962)).

15D. 1-Anthracenecarbaldehyde

To a 2 L round bottom flask equipped with condenser and magentic stirring bar was added (1-anthracenyl)methanol (15C, 21.0 g, 0.10 mol), CH$_2$Cl$_2$ (1200 mL) and pyridinium chlorochromate (PCC) (Aldrich, 32.33 g, 0.15 mol). The mixture was then refluxed for 5 h. The reaction was cooled and then filtered through a plug of silica gel (400 g) using PhCH$_3$ as eluting solvent. The first 1 L of solution was collected and concentrated to give 16 g of crude product. This material was further purified by preparative HPLC using PhCH$_3$ as eluting solvent. The solvent was removed and the resulting solid recrystallized (PhCH$_3$/hexane) to give 14.0 g (67%) of 1-anthracenecarbaldehyde mp 130°–131.5°, (C, H), (lit. mp 126.5°–127.5°, P. H. Gore *J. Chem. Soc.* 1616 (1959)).

15E. 2-((1-Anthracenylmethyl)amino)-2-methyl-1,3-propanediol hydrochloride

Using the reductive amination procedure outlined in 1, 1-anthracenecarbaldehyde (15D) and 2-amino-2-methyl-1,3-propanediol (Aldrich) gave 2-((1-anthracenylmethyl)amino)-2-methyl-1,3-propanediol hydrochloride mp 189°–191° (dec), (EtOH/Et$_2$O), (C, H, Cl, N).

EXAMPLE 16

2-(((10-Bromo-1-anthracenyl)methyl)amino-2-methyl-1,3-propanediol

16A. (10-Bromo-1-anthracenyl)methanol

10-Bromo-1-anthracenecarboxylic acid made from 1-anthracenecarboxylic acid (15B) by the procedure of E. Barnett, J. W. Cook, and H. H. Grainger, *Ber.* 57 B, 1775 (1924), was reduced with BH$_3$ in THF by the procedure outlined in 15C to give (10-bromo-1-anthracenyl)methanol mp 125°–127°, (EtOAc/hexane), (C, H, Br).

16B. 10-Bromo-1-anthracenecarbaldehyde

Using the procedure outlined in 15D, oxidation of (10-bromo-1-anthracenyl)methanol (16A) with pyridinium chlorochromate (Aldrich) gave 10-bromo-1-anthracenecarbaldehyde mp 134.5°–135.5°, (PhCH$_3$/hexane), (C, H, Br).

16C. 2-(((10-Bromo-1-anthracenyl)methyl)amino)-2-methyl-1,3-propanediol hydrochloride Using the reductive amination procedure outlined in 1, 10-bromo-1-anthracenecarbaldehyde (16B) and 2-amino-2-methyl-1,3-propanediol (Aldrich) gave 2-(((10-bromo-1-anthracenyl)methyl)amino)-2-methyl-1,3-propanediol hydrochloride mp 225°–226.5° (dec), (EtOH/Et$_2$O), (C, H, Br, Cl, N).

EXAMPLE 17

2-(((2-Chloro-9-anthracenyl)methyl)amino)-2-methyl-1,3-propanediol

17A. 2-Chloro-9-anthracenecarbaldehyde and
17B. 3-chloro-9-anthracenecarbaldehyde 2-Chloroanthracene prepared from 2-chloroanthraquinone (Aldrich) by the method of H. O. House et al. (*J. Org. Chem.* 38 1167 (1973)) was formylated by the method of A. Reiche et al., *Chem Ber.* 93, 88 (1960) to give a (4:1) mixture of 2- and 3-chloro-9-anthracenecarbaldehydes (87%). Trituration of the material with CH$_3$OH gave preferential crystallization of 2-choro-9-anthracenecarbaldehyde, which after further crystallization (PhCH$_3$/hexane) gave the pure 2-isomer mp 149°–150° (C, H, Cl) (lit. 148°–150°, British Pat. No. 1,149,557). The filtrate (R$_f$=0.59, SiO$_2$, PhCH$_3$) from the CH$_3$OH trituration was further purified by preparative HPLC to give pure 3-chloro-9-anthracenealdehyde mp 122°–123.5°, (PhCH$_3$/hexane), (C, H, Cl), R$_f$=0.48, SiO$_2$, PhCH$_3$).

17C. 2-(((2-Chloro-9-anthracenyl)methyl)amino)-2-methyl-1,3-propanediol hydrochloride Using the reductive amination procedure outlined in 1, 2-chloro-9-anthracenecarbaldehyde (17A) and 2-amino-2-methyl-1,3-propanediol gave 2-(((2-chloro-9-anthracenyl)methyl)amino-2-methyl-1,3-propanediol hydrochloride mp 265°–266° (dec), (CH$_3$OH/Et$_2$O), (C, H, Cl, N).

EXAMPLE 18

2-(((3-Chloro-9-anthracenyl)methyl)amino-2-methyl-1,3-propanediol hydrochloride Using the reductive amination procedure outlined in 1, 3-chloro-9-anthracenecarbaldehyde (17B) and 2-amino-2-methyl-1,3-propanediol (Aldrich) gave 2-(((3-chloro-9-anthracenyl)methyl)amino)-2-methyl)-1,3-propanediol hydrochloride mp 268°–269° (dec), CH$_3$OH/Et$_2$O, (C, H, Cl, N).

EXAMPLE 19

2-(((10-Ethylthio-9-anthracenyl)methyl)amino)-2-methyl-1,3-propanediol hydrochloride

19A. 10-Ethylthio-9-anthracenecarbaldehyde

Using the procedure described in 3A, 10-chloro-9-anthracenecarbaldehyde (Aldrich) and ethyl iodide (Fisher) gave an oil which solidified to give 10-ethylthio-9-anthracenecarbaldehyde mp 74°–75.5° (C, H, S).

19B. 2-(((10-Ethylthio-9-anthracenyl)methyl)amino)-2-methyl-1,3-propanediol hydrochloride Using the reductive amination procedure outlined in 1, 10-ethylthio-9-anthracenecarbaldehyde (19A) and 2-amino-2-methyl-1,3-propanediol (Aldrich gave 2-(((10-ethylthio-9-anthracenyl)methyl)amino)-2-methyl-1,3-propanediol hydrochloride, mp 201°–202°, (EtOH/Et$_2$O), (C, H, Cl, N, S).

EXAMPLE 20

2-(((10-(2-Hydroxyethylthio)-9-anthracenyl)methyl)amino)-2-methyl-1,3-propanediol

20A. 10-((2-Hydroxyethyl)thio)-9-anthracenecarbaldehyde

Using the procedure described in 3A (except that the alkylation reaction was run for 1 h at 65°) 10-chloro-9-anthracenecarbaldehyde (Aldrich) and 2-iodoethanol (Aldrich) gave 10-((2-hydroxyethyl)thio)-9-anthracenecarbaldehyde mp 103°–104°, (PhCH$_3$/hexane), (C, H, S).

20B. 2-(((10-(2-Hydroxyethylthio)-9-anthracenyl)methyl)amino)-2-methylpropanediol hydrochloride Using the reductive amination procedure described in 1, 10-((2-hydroxyethyl)thio)-9-anthracenecarbaldehyde (20A) and 2-amino-2-methyl-1,3-propanediol (Aldrich) gave 2-(((10-(2-hydroxyethylthio)-9-anthracenyl)methyl)amino)-2-methyl-1,3-propanediol hydrochloride, mp 199°–200° (dec), EtOH/Et$_2$O), (C, H, Cl, N, S).

EXAMPLE 21

2-(((10-Chloro-9-anthracenyl)methyl)amino)-2-hydroxymethyl-1,3-propanediol hydrochloride Using the reductive amination procedure described in 1, 10-chloroanthracene-9-carbaldehyde (Aldrich) and tris(hydroxymethyl)aminomethane (Aldrich) gave 2-(((10-chloro-9-anthracenyl)methyl)amino)-2-hydroxymethyl-1,3-propanediol hydrochloride, mp 251°–254° (dec), (EtOH/Et$_2$O), (C, H, Cl, N).

EXAMPLE 22

2-(((2,10-Dichloro-9-anthracenyl)methyl)amino)-2-methyl-1,3-propanediol

EXAMPLE 23

2-(((3,10-Dichloro-9-anthracenyl)methyl)amino)-2-methyl-1,3-propanediol 22A. 2,10-Dichloroanthracenecarbaldehyde and 22B. 3,10-Dichloro-9-anthracenecarbaldehyde Using the procedure of V. I. Rogovik et al. (*Zh. Org. Khim.* 3, 1315 (1967)) 2-chloroanthraquinone (Aldrich) gave a mixture (1:1) of 2,10- and 3,10-dichloroanthracenecarbaldehydes (68%). A portion of the mixture was separated by preparative HPLC using the shave/recycle technique to give 2,10-dichloro-9-anthracenecarbaldehyde mp 175.5°–176.5°, (PhCH$_3$), (C, H, Cl), and 3,10-dichloro-9-anthracenecarbaldehyde mp 173.5°–175°, (PhCH$_3$), (C, H, Cl). The remainder of the material was used as a mixture.

22C. 2-(((2,10-Dichloro-9-anthracenyl)methyl)amino)-2-methyl-1,3-propanediol hydrochloride 23. 2-(((3,10-Dichloro-9-anthracenyl)methyl)amino)-2-methyl-1,3-propanediol hydrochloride Using the reductive amination procedure outlined in 1, the mixture of 2,10- and 3,10-dichloro-9-anthracenecarbaldehydes (22A+22B) and 2-amino-2-methyl-1,3-propanediol (Aldrich) gave after workup a mixture of 2-(((2,10- and 3,10-dichloro-9-anthracenyl)methyl)amino)-2-methyl-1,3-propanediols. These two compounds were separated by preparative HPLC using the shave/recycle technique with EtOAc as the eluting solvent to give after treatment with 1M ethanolic HCl, 2-(((2,10-dichloro-9-anthracenyl)methyl)amino)-2-methyl-1,3-propanediol hydrochloride mp 305°–306° (dec), (CH$_3$OH/Et$_2$O), (C, H, Cl, N), (R$_f$=0.53, SiO$_2$, EtOAc) and 2-(((3,10-dichloro-9-anthracenyl)methyl)amino)-2-methyl-1,3-propanediol hydrochloride mp 303°–304° (dec), (CH$_3$OH/Et$_2$OH), (C, H, Cl, N), (R$_f$=0.39, SiO$_2$, EtOAc).

EXAMPLE 24

2-(((10-Ethoxy-9-anthracenyl)methyl)amino)-2-methyl-1,3-propanediol 24A. 10-Ethoxy-9-anthracenecarbaldehyde Using the procedure outlined in 13A, except that NaOEt (Aldrich)/EtOH was used instead of NaOCH$_3$/CH$_3$OH, 10-chloro-9-anthraldehyde (Aldrich) gave 10-ethoxy-9-anthracenecarbaldehyde mp 88°–90°, (CH$_2$Cl$_2$/hexane) (C, H).

24B. 2-(((10-Ethoxy-9-anthracenyl)methyl)amino)-2-methyl-1,3-propanediol hydrochloride Using the reductive amination procedure outlined in 1, 10-ethoxy-9-anthracenecarbaldehyde (24A) and 2-amino-2-methyl-1,3-propanediol (Aldrich) gave 2-(((10-ethoxy-9-anthracenyl)methyl)amino)-2-methyl-1,3-propanediol hydrochloride mp 229°–230° (dec), (EtOH/Et$_2$O), (C, H, Cl, N).

EXAMPLE 25

2-((10-(2-Hydroxyethyloxy)-9-anthracenylmethyl)amino)-2-methyl-1,3-propanediol 25A. 10-(2-Hydroxyethoxy)-9-anthracenecarbaldehyde A 3 L 2-neck flask fitted with thermometer, condenser, stirring bar, N$_2$-line and bubbler was charged with KOtBu (MCB, 25 g, 0.22 mol), 1,2-ethylene glycol (Fisher, 1.5 L) and 10-chloro-9-anthraldehyde (Aldrich), 50 g, 0.207 mol). The mixture was stirred at 100° for 1.5 h. An additional 5 g (45 mmol) of KOtBu was added and the stirring continued for an additional 0.5 h. The reaction mixture was cooled poured into cold H$_2$O (1.5 L), then stirred for 10 min before the precipitate was collected by filtration. The yellow solid was dissolved in CH$_2$Cl$_2$ (1 L) and passed through a plug of SiO$_2$ (100 g), using CH$_2$Cl$_2$ (9 L) as the eluting solvent. The CH$_2$Cl$_2$ contained impurities only and was discarded. The desired material was then eluted with EtOAc (12 L). The appropriate fractions were combined and the solvent removed to give (after drying at 50°) 28.82 g (53%), 10-(2-hydroxyethyloxy)-9-anthracenecarbaldehyde mp 142°–144°, (CH$_2$Cl$_2$/hexane), (C, H).

25B. 2-(((10-(2-Hydroxyethoxy)-9-anthracenyl)methyl)amino)-2-methyl-1,3-propanediol hydrochloride Using the reductive amination procedure outlined in 1, 10-(2-hydroxyethoxy)-9-anthracenecarbaldehyde (25A) and 2-amino-2methyl-1,3-propanediol (Aldrich) gave 2-(((10-(2-hydroxyethoxy)-9-anthracenyl)methyl)amino)-2-methyl-1,3-propanediol hydrochloride ½H$_2$O 1/10EtOH mp 179°–181° (dec), (EtOH/Et$_2$O), (C, H, N, Cl).

The free base of this compound (prepared by neutralization with NaOH can be used to make various acid addition salts such as the methanesulfonate salt.

EXAMPLE 26

2-Methyl-2-(((10-methylsulfonyl-9-anthracenyl)methyl)amino)-1,3-propanediol 26A. 10-Methylsulfonyl-9-anthracenecarbaldehyde 10-Methylthio-9-anthracenecarbaldehyde (3A, 4.50 g, 17.83 mmol) was dissolved in CH$_2$Cl$_2$ (100 mL) and cooled to 0° in an ice bath. To the magnetically stirred solution was added dropwise over 15 min a solution of m-chloroperbenzoic acid (Aldrich (85%), 7.08 g, 35.76 mmol) in 250 mL of CH$_2$Cl$_2$. The ice bath was removed and the clear solution stirred for 2 h. The solution was then sequentially washed with 10% Na$_2$S$_2$O$_3$ solution (500 mL) and satd. Na$_2$CO$_3$ solution (2×100 mL). The solvent was removed, and the crude material passed through a small plug of SiO$_2$ (200 g) using CH$_2$Cl$_2$ (500 mL) as the eluting solvent. The solvent was removed to give the crude product which was recrystallized from CH₂Cl₂/EtOH to give 10-methylsulfonyl-9-anthracenecarbaldehyde mp 216°–217° (C, H, S).

26B.

2-Methyl-2-(((10-methylsulfonyl-9-anthracenyl)methyl)amino)-1,3-propanediol hydrochloride Using the reductive amination procedure outlined in 1, 10-methylsulfonylanthracene-9-carbaldehyde (26A) and 2-amino-2-methyl-1,3-propanediol (Aldrich) gave 2-methyl-2-(((10-methylsulfonyl-9-anthracenyl)methyl)amino)-1,3-propanediol hydrochloride mp 238°–239° (dec), (CH₃OH/Et₂O), (C, H, Cl, N, S).

EXAMPLE 27

2-(((10-(2-Methoxyethoxy)-9-anthracenyl)methyl)amino)-2-methyl-1,3-propanediol 27A. 10-(2-Methoxyethoxy)-9-anthracenecarbaldehyde A mixture of KOtBu (MCB, 18.2 g, 0.162 mol)) in 2-methoxyethanol (1 L) was treated with 10-chloro-9-anthraldehyde (Aldrich, 25 g, 0.104 mol) and refluxed for 2 h. The cooled reaction mixture was diluted with H₂O (5 L), and the resulting oil stirred for 2 h until solidification occurred. The filtered solid was chromatographed on a plug of SiO₂ (500 g) using CH₂Cl₂ as the eluting solvent to afford 26.9 g (92%) of 10-(2-methoxyethoxy)-9-anthracenecarboxaldehyde mp 87°–88°, (C, H), (CH₂Cl₂/hexane).

27B.

2-(((10-(2-Methoxyethoxy)-9-anthracenyl)methyl)amino)-2-methyl-1,3-propanediol hydrochloride ¼H₂O Using the reductive amination procedure outlined in 2B, (10-methoxyethoxy)anthracene-9-carbaldehyde (27A) and 2-amino-2-methyl-1,3-propanediol gave 2-(((10-(2-methoxyethoxy)-9-anthracenyl)methyl)amino)-2-methyl-1,3-propanediol hydrochloride.¼H₂O mp 182°–183° (dec), (EtOH/Et₂O), (C, H, Cl, N).

EXAMPLE 28

2-Methyl-2-((((10-N-morpholino)-9-anthracenyl)methyl)amino)-1,3-propanediol 28A. 10-(N-Morpholino)-9-anthracenecarbaldehyde 10-Chloro-9-anthracenecarbaldehyde (Aldrich, 25 g, 0.104 mol) in morpholine (MCB, practical, 500 mL) was heated at 55° under N₂ for 17 h. The reaction mixture was poured into H₂O (2 L). A precipitate formed which was filtered and then chromatographed on a plug of SiO₂ (1 kg) using PhCH₃ (4 L) as the initial eluting solvent to remove starting material and byproducts. The orange product band was then eluted with CH₂Cl₂ (2 L) to give after removal of solvent 10.58 g (35%) of 10-N-morphilino)-9-anthracenecaerboxaldehyde mp 182°–184° (softens 175°), (C, H, N).

28B.

2-Methyl-2-((((10-N-morpholino)-9-anthracenyl)methyl)amino)-1,3-propanediol methanesulfonate.¾H₂O Using the reductive amination procedure outlined in 2B, 10-(N-morpholino)-9-anthracenecarbaldehyde (28A) 2-amino-2-methyl-1,3-propanediol gave 2-((((10-N-morpholino)-9-anthracenyl)methyl)amino)-1,3-propanediol methanesulfonate ¾H₂O mp 159°–160° (dec), (EtOH/Et₂O), (C, H, N, S).

EXAMPLE 29

2-(((10-(1H-Imidazol-1-yl)-9-anthracenyl)methyl)amino)-2-methyl-1,3-propanediol 29A. 10-(1-H̲-Imidazol-1-yl)-9-anthracencarbaldehyde A solution of 10-chloro-9-anthraldehyde (Aldrich, 15 g, 0.062 mol), imidazole (Aldrich, 10.2 g, 0.15 mmol) and DMF (300 mL) was warmed to 55° and treated with KOtBu (MCB, 7.0 g, 0.07 mol) and stirred for 30 min. The reaction mixture was poured into 0.1N NaOH (1.5 L). The precipitate was filtered and then chromatographed on a plug of SiO₂ (500 g) using CH₂Cl₂ (3 L) as the initial eluting solvent to remove starting material and byproducts. The yellow product band was then eluted with EtOAc (2 L) to yield, after removal of solvent and drying, 12.29 g (73%) of 10-(1H-imidazol-1-yl)-9-anthracenecarbaldehyde mp 194°–196°, (C, H, N), (EtOAc).

29B.

2-(((10-(1H-Imidazol-1-yl)-9-anthracenyl)methyl)amino)-2-methyl-1,3-propanediol hydrochloride 11/10 H₂O Using the reductive amination procedure outlined in 2B, 10(1H-imidazol-1-yl)-9-anthracenecarbaldehyde (29A) and 2-amino-2-methyl-1,3-propanediol (Aldrich) gave 2-(((10-(1H-imidazol-1-yl)-9-anthracenyl)methyl)amino)-2-methyl-1,3-propanediol hydrochloride.11/10 H₂O mp 212°–215° (dec), (EtOH/Et₂O), (C, H, Cl, N).

EXAMPLE 30

(+ −)(2R*,3S*)-2-((9-Anthracenylmethyl)amino)-2-methyl-1,3-butanediol 30A. (+ −)(2R*,3S*)-2-Methyl-2-nitro-1,3-butanediol and 30B. (+ −)(2R*,3R*)-2-Methyl-2-nitro-1,3-butanediol To a mixture of 2-nitro-1-propanol (Aldrich, 63.0 g, 0.60 mol) and acetaldehyde (Eastman, 39.6 g, 0.90 mol) cooled in an ice bath under N₂ was added cold H₂O (40 mL) and calcium hydroxide (200 mg). The mixture was allowed to warm to RT over 2 h and then stirred for 68 h. The resulting solution was neutralized with excess solid CO₂. The mixture was stirred for 1 h before filtration through a Millipore ® filter. The filtrate was then concentrated under vacuum at 35°. The residue, a viscous syrup partially crystallized on drying under vacuum (0.1 mm, RT, 48 h) was then triturated with cold Et₂O (35 mL). Solid white crystals which formed were collected by filtration, washed with cold Et₂O (3×15 mL) and dried under vacuum (0.1 mm, RT) to give 34.1 g of material, judged by NMR to be (+ −)(2R*,3S*)-2-methyl-2-nitro-1,3-butanediol (30A) (purity >97%, racemic). After recrystallization, the diastereomeric purity was >99%, mp 78.5°–81° (lit. 78°; cf. *Beil* 1, 482, in Henry, *Bull. Soc. Chim. Fr.* [3] 15, 1224), (C, H, N).

The original filtrate (including washes) was concentrated under vacuum to a pale yellow liquid which was subjected to flash chromatography as follows: The sample was mixed with hexane/EtOAc (2:1, 100 mL) and added to a column of dry SiO₂ (1.5 kg). The column was eluted with hexane/EtOAc (2:1, 12 L) then hexane/EtOAc (1:1, 6 L) while 500 mL fractions were collected. Appropriate fractions were combined. Pure product was found in the final 8 L; yield, 38.7 g of viscous syrup, judged by NMR to be a 1:1 mixture of the two racemic diastereomers (30A and 30B), (C, H, N).

This and another batch of the 1:1diasteriomeric mixture of 30A and 30B (prepared as described above) were combined (67 g, total) and subjected to successive liquid-liquid partitioning between H$_2$O and EtOAc to give pure samples (99% on the basis of NMR and HPLC (Hamilton PRP-1 column using 3.5% aqueous acetonitrile as the mobile phase) of (+−)(2R*,3S*)-2-methyl-2-nitro-1,3-butanediol (30A) (24.9 g, k'=4,3 mp 79°–81°, C,H,N) and (+−)(2R*,3R*)-2-methyl-2-nitro-1,3-butanediol (30B) (15.8 g, k'=2.1, C, H, N, a colorless, viscous liquid).

30C.
(+−)(2R*,4S*,5R*)-4,5-dimethyl-5-nitro-2-phenyl-1,3-dioxane and

30D.
(+−)(2R*,4S*,5S*)-4,5-dimethyl-5-nitro-2-phenyl-1,3-dioxane

The relative configurations of the two diasteriomeric pairs (30A and 30B) were unequivocably assigned on the basis of comparative NMR analysis of the respective cyclic acetals derived from benzaldehyde. Thus, 30A (1.49 g, 0.01 mol) and benzaldehyde (Mallinckrodt, 1.06 g, 0.01 mol) were condensed in benzene in the presence of a catalytic amount of p-toluenesulfonic acid (Fisher) with azeotropic removal of water (according to the method of H. Piotrowska, B. Serafin and T. Urbanski, *Tetrahedron* 109, 379 (1963)). After successive washing with satd. NaHCO$_3$ solution, drying (MgSO$_4$), filtration, and removal of the benzene by rotary evaporation, a pale yellow solid was obtained. A solution of this product in ethanol at 0° C. provided an oil which was isolated by decanting the mother liquor and drying under vacuum (0.1 mm, RT). The yield was 1.48 g (62%) of (+−)(2R*,4S*,5R*)-4,5-dimethyl-5-nitro-2-phenyl-1,3-dioxane (30C) (C, H, N).

Similarly prepared from 30B and benzaldehyde was (+−)(2R*,4S*,5S*)-4,5-dimethyl-5-nitro-2-phenyl-1,3-dioxane (30D)(74%) (C, H, N).

30E.
(+−)(2R*,3R*)-2-Amino-2-methyl-1,3-butanediol acetate

To a solution of (+−)(2R*,3R*)-2-methyl-2-nitro-1,3-butanediol (30B, 22.1 g, 0.148 mol) in 95% EtOH (150 mL) was added glacial acetic acid (25 mL) and 10% Pd/C (MCB, 2.0 g). The reduction was carried out in a Parr apparatus at 50 psi of H$_2$ during a 48 h period at RT. The catalyst was removed by filtration through a Millipore* filter, and the solvent removed under vacuum (2 days). The viscous, colorless syrup was dissolved in abs. EtOH (30 mL). Dilution with abs. Et$_2$O (300 mL) gave a cloudy liquid which was placed in a refrigerator for two days. During this time, colorless crystals formed. They were washed with Et$_2$O and dried in a vacuum oven at RT for two days. The yield of (+−)(2R*,3R*)-2-amino-2-methyl-1,3-butanediol acetate was 25.6 g (97%) mp 117°–121°, (C, H, N).

30F. (+−)(2R*,3S*)-2-Amino-2-methyl-1,3-butanediol acetate

Using the procedure described for 30E (+−)(2R*,3S*)-2-methyl-2-nitro-1,3-butanediol (30A) gave (+−)(2R*,3S*)-2-amino-2-methyl-1,3-butanediol acetate (93%) mp 163°–165° (C, H, N).

30G.
(+−)(2R*,3S*)-2-((9-Anthracenylmethyl)amino)-2-methyl-1,3-butanediol hydrochloride ¼H$_2$O To a RB flask was added (+−)(2R*,3S*)-2-amino-2-methyl-1,3-butanediol acetate (30F) and an equimolar amount of sodium methoxide (MCB) and enough CH$_2$OH to a solution upon warming. The solvent was removed by rotary evaporation and after addition of anthracene-9-carbaldehyde (Aldrich) the reaction run following the normal reductive amination outlined in 2B to give (+−)(2R*,3S*)-2-((9-anthracenylmethyl)amino)-2-methyl-1,3-butanediol hydrochloride.¼H$_2$O mp 216°–217° (dec), (EtOH/Et$_2$O), (C, H, Cl, N).

EXAMPLE 31

2-(((2-Ethyl-9-anthracenyl)methyl)amino)-2-methyl-1,3-propanediol and
2-(((3-ethyl-9-anthracenyl)methyl)amino)-2-methyl-1,3-propanediol 31A. 2-Ethylanthracene To a 5 L 3-neck flask fitted with condenser, thermometer, and overhead stirrer was added 2-ethylanthraquinone (Aldrich, 120 g, 0.51 mmol), Zn dust (Mallinckrodt, 300 g, 4.59 mol), CuSO$_4$.5H$_2$O (Mallinckrodt, 3.0 g) and 28% NH$_4$OH (Mallinckrodt, 2.8 mL). The temperature was increased until the initial dark red color had faded (about 6 h). The reaction mixture was then filtered. The filtrate was extracted with EtOAc (5×1 L), and the filter cake washed with EtOAc (2×1 L). The EtOAc solutions were combined and the solvent removed. The residue was refluxed with a mixture of conc. HCl (10 mL) in i-PrOH (1.2 L) for 2 h. Upon cooling, a solid precipitated which was filtered, washed with abs. EtOH (100 mL) and dried to give 40 g (38%) of 2-ethylanthracene mp 140°–142°, (lit. mp 148°–150°, L. H. Klemm et al., *J. Org. Chem.* 28, 625 (1983), (C, H).

31B. 2- and 3-Ethylanthracene-9-carbaldehyde

2-Ethylanthracene (31A, 40 g, 0.194 mol) was formylated using the method of A. Rieche et al., *Chem. Ber.* 93, 88 (1980) to give a crude mixture of aldehydes. Chromatography over a plug of SiO$_2$ (500 g) with PhCH$_3$ as the eluting solvent gave 43.68 g (96%) of a mixture of 2- and 3-ethylanthracene-9-carbaldehyde, as an oil, which was used without further purification.

31C.
2-(((2-Ethyl-9-anthracenyl)methyl)amino)-2-methyl-1,3-propanediol and
2-(((3-ethyl-9-anthracenyl)methyl)amino)-2-methyl-1,3-propanediol hydrochloride.¼H$_2$O Using the reductive amination procedure outlined in 1, the mixture of 2- and-3-ethylanthracene-9-carbaldehyde (31B) and 2-amino-2-methyl-1,3-propanediol (Aldrich) gave a mixture of 2-(((2-ethyl-9-anthracenyl)methyl)amino)-2-methyl-1,3-propanediol and 2-(((3-ethyl-9-anthracenyl)methyl)amino)-2-methyl-1,3-propanediol hydrochloride.¼H$_2$O mp 203°–205° (dec), (EtOH/Et$_2$O), (C, H, Cl, N)

EXAMPLE 32

2-((9-Anthracenylmethyl)amino)-2-ethoxymethyl-1,3-propanediol

32A.
3,5-Diphenyl-7a(7H)-ethoxymethyl-1H,3H,5H-oxazolo(3,4-c)oxazole

A mechanically stirred 60% dispersion of NaH in mineral oil (Alfa, 34.0 g, 0.85 mol) was washed with dry hexane to remove the oil and suspended in dry DMF (300 mL). To the mixture was added a solution of 3,5-diphenyl-1H,3H,5H-oxazolo(3,4-c)oxazole-7a(7H)-methanol (208.2 g, 0.7 mol, prepared by the method of J. Pierce et al., *J. Amer. Chem. Soc.* 73 2595 (1951)) in dry DMF (300 ml) keeping the reaction mixture between 30°–35°. The salt suspension was stirred at RT for 60 min, diluted with dry DMF (200 mL) to facilitate stirring, cooled, then treated with ethyl iodide (Aldrich, excess) at such a rate that the reaction temperature was between 20°–35°. The mixture was stirred at RT for 2 h, then cautiously treated with abs. EtOH (30 mL). The resulting mixture was diluted with $Et_2O$ (2.5 L) and the resulting solids removed by filtration. The solvent was then removed using a rotary evaporator to give 229.5 g of a yellow oil containing both starting material and desired product. A solution of the oil in chloroform was mixed with $SiO_2$ (200 g) and the solvent removed. The solid was then added to a column of $SiO_2$ (800 g). Elution with the EtOAc/hexane (1:3.5) gave 139.7 g (61.3%) of 3,5-diphenyl-7a(7H)-ethoxymethyl-1H,3H,5H-oxazolo(3,4-c)oxazole. An analytical sample was obtained by recrystallization from hexane, mp 83.5°–85°, (C, H, N). The bulk of the material was used without further purification.

32B. 2-Amino-2-ethoxymethyl-1,3-propanediol hydrochloride.¼$H_2O$ 3,5-Diphenyl-7a(7H)-ethoxymethyl-1H,3H,5H-oxazolo(3,4-c)oxazole (32A, 136 g, 0.42 mol) was dissolved in 6N HCl (400 mL) and the resulting solution stirred 1.5 h at RT. After extraction with $Et_2O$ (2×200 mL) to remove benzaldehyde, the aqueous solution was concentrated on a rotary evaporator to give a colorless oil. This was cooled in an ice bath to facilitate crystallization. The solid which formed was slurried with cold $CH_3CN$, filtered, then washed with $Et_2O$ and dried in a vacuum oven at RT to give 71 g (89%) of 2-amino-2-ethoxymethyl-1,3-propanediol hydrochloride.¼$H_2O$ mp 78°–79°, (C, H, Cl, N).

32C.
2-((9-Anthracenylmethyl)amino)-2-ethoxymethyl-1,3-propanediol hydrochloride To a RB flask was added 2-amino-2-ethoxymethyl-1,3-propanediol hydrochloride.¼$H_2O$ (32B) and an equimolar amount of sodium methoxide (MCB) and enough $CH_3OH$ to give a solution when warmed. The solvent was then removed by rotary evaporation, and the reaction run following the normal reductive amination procedure outlined in 2B to give 2-((9-anthracenylmethyl)amino)-2-ethoxymethyl-1,3-propanediol hydrochloride mp 176.5°–178.5°, (EtOH/$Et_2O$), C, H, Cl, N.

EXAMPLE 33

2-((9-Anthracenylmethyl)amino)-3-methoxy-2-methyl-1-propanol

33A.
4-Aza-3-hydroxymethyl-3-methyl-1-oxaspiro[4.5]decane

A solution of 2-amino-2-methyl-1,3-propanediol (Aldrich, 303.4 g, 3.0 mol), cyclohexanone (Fisher, 294.5 g, 3.0 mol) and $PhCH_3$ (400 mL) was refluxed for approximately 2 h with azeotropic removal of $H_2O$. The material which crystallized from the $PhCH_3$ on cooling was recrystallized 2× from hexane to give 444.4 g of 4-aza-3-hydroxymethyl-3-methyl-1-oxaspiro[4.5]decane (80%) mp 52°–54°, (C, H, N).

33B.
4-Aza-3-methoxymethyl-3-methyl-1-oxaspiro[4.5]decane

A mechanically stirred 60% dispersion of NaH in mineral oil (Alfa, 75 g, 1.9 mol) was washed with dry hexane to remove the oil and suspended in dry DMF (200 mL). To the mixture was added a solution of 4-aza-3-hydroxymethyl-3-methyl-1-oxaspiro[4.5]decane (33A, 27.8 g, 1.5 mol) in dry DMF (200 mL) keeping the reaction mixture temperature between 30°–35°. Small amounts of DMF were added as necessary to facilitate stirring. The mixture was stirred at RT for 1.5 h, then cooled and treated with methyl iodide (Fisher, 234.2 g, 102.7 mL, 1.65 mol) keeping the reaction temperature between 20°–30°. The mixture was stirred 2 h at RT and slowly treated with abs. EtOH (40 mL), then diluted with dry $Et_2O$ (3 L). The reaction mixture was filtered, and the solvent removed by rotary evaporation. The residue was then fractionally distilled to give 200.7 g (70.3%) of 4-aza-3-methoxymethyl-3-methyl-1-oxaspiro[4.5]decane as a colorless liquid bp 114°/14 mm, (C, H, N).

33C. 2-Amino-3-methoxy-2-methyl-1-propanol

A solution of 4-aza-3-methoxymethyl-3-methyl-1-oxaspiro[4.5]decane (33B, 299 g, 1.5 mol) and 6N HCl (500 mL) was refluxed for 60 min. On cooling, to layers formed, the upper one containing cyclohexanone was removed by extraction with $Et_2O$ (2×400 mL). The lower aqueous layer was concentrated on a rotary evaporator to give a syrup which then was treated with excess 50% NaOH. The resulting slurry was extracted with $Et_2O/CH_2Cl_2$ (2:1, 4×500 mL), then with $CH_2Cl_2$ (500 mL). The solvent was removed by rotary evaporation to give 198 g of pale oil. Fractional distillation of this oil gave 166 g (93%) of 2-amino-3-methoxymethyl-1-propanol as a colorless oil bp 94° C./17 mm, (C, H, N).

33D.
2-((9-Anthracenylmethyl)amino)-3-methoxy-2-methyl-1-propanol hydrochloride Using the reductive amination procedure outlined in 1, anthracene-9-carbaldehyde (Aldrich) and 2-amino-3-methoxy-2-methyl-1-propanol (33C) gave 2-((9-anthracenylmethyl)amino)-3-methoxy-2-methyl-1-propanol hydrochloride mp 214°–215° (dec), (EtOH/$Et_2O$), (C, H, Cl, N).

EXAMPLE 34

(1α,2β,3α)-2-(9-Anthracenylmethyl)amino)-1,3-cyclohexanediol

34A. 1α,2β,3α-2-Amino-1,3-cyclohexanediol acetate

This compound was prepared by the method of F. Lichtenthaler (*Ber.* 96, 845 (1963)), mp 175°–177°, (C, H, N), (lit. 178°–179°, F. Lichtenthaler, (*Ber.* 96, 851 (1963)).

34B. (1α,2β,3α)-2-((9-Anthracenylmethyl)amino)-1,3-cyclohexanediol methanesulfonate To a RB flask was added (1α,2β,3α)-2-amino-1,3-cyclhexanediol acetate (34A) and an equimolar amount of NaOCH$_3$ (MCB) and enough CH$_3$OH to give a solution upon warming. The solvent was removed by rotary evaporation, and after addition of 9-anthracenecarbaldehyde the reaction run following the reductive amination outlined in 2B to give (1α,2β,3α)-2-((9-anthracenylmethyl)amino)-1,3-cyclohexanediol methanesulfonate mp 251°–252° (dec), (CH$_3$OH/Et$_2$O), (C, H, N, S).

EXAMPLE 35

2-((9-Anthracenylmethyl)amino)-2-isopropyl-1,3-propanediol

35A. 2-Isopropyl-2-nitro-1,3-propanediol

A solution of 2-methyl-1-nitropropane (38.7 g, 0.375 mol, prepared by the procedure of N. Kornblum, B. Tunbe, and H. Ungnade, *J. Amer. Chem.Soc.*, 76, 3209 (1954)) and NEt$_3$ (Eastman, 3.79 g, 0.375 mol) in CH$_3$OH (50 mL) was added dropwise 37% aqueous formaldehyde solution (Mallinckrodt, 76.2 g, 0.938 mol) at a rate such that the reaction mixture temperature did not exceed 30°. After 72 h, the solution was concentrated under vacuum and the residue was dissolved in H$_2$O (250 mL). The solution was continuously extracted for 1 h with CH$_2$Cl$_2$ (1 L). The CH$_2$Cl$_2$ solution was dried (MgSO$_4$), filtered, and concentrated to give 53.3 g (87%) of 2-isopropyl-2-nitro-1,3-propanediol, as a waxy, white solid mp 67°–72° C. (lit. mp 87°–88° B. M. Vanderbilt and H. B. Hass, *Ind. Eng. Chem.* 32, 34 (1940). In our hands this procedure failed to give the desired compound).

35B. 2-Amino-2-isopropyl-1,3-propanediol acetate.¼H$_2$O

Using the procedure in 30E, 2-isopropyl-2-nitro-1,3-propanedil (52A) gave a 98% yield of 2-amino-2-isopropyl-1,3-propanediol acetate.¼H$_2$O mp 155°–155.5°. H. S. Broadbent et al., *J. Heterocyclic Chem.*, 13, 337 (1975) report the synthesis of this compound as the free base (mp 70°–72°)).

35C. 2-((9-Anthracenylmethyl)amino)-2-isopropyl-1,3-propanediol methanesulfonate To a RB flask was added 2-amino-2-isopropyl-1,3-propanediol acetate.¼H$_2$O (35B) and an equimolar amount of NaOCH$_3$ (MCB) and enough CH$_3$OH to give a solution when warmed. The solvent was removed by rotary evaporation and after addition of 9-anthracenecarbaldehyde (Aldrich) the reaction run following the normal reductive amination procedure outlined in 2B to give 2-((9-anthracenylmethyl)amino)-2-isopropyl-1,3-propanediol methane-sulfonate mp 192°–194° (dec), (EtOH/Et$_2$O), (C, H, N, S).

EXAMPLE 36

2-((9-Anthracenylmethyl)amino)-2-methyl-1,4-butanediol

36A. Ethyl N-benzylidene-1-alaninate

Ethyl N-benzylidene-1-alaninate was prepared according to the general procedure of G. Stork et al., *J. Org. Chem.* 41 349 (1976), bp 98°–100°/0.4 mm (lit. 100°/0.3 mm, A. Calcagni et al., Synthesis 445 (1981)).

36B. 2-(2-Iodoethoxy)tetrahydro-2-H-pyran

Freshly distilled dihydropyran (Aldrich, 59.0 g, 0.7 mol) was added dropwise to a cooled solution of 2-iodoethanol (Aldrich, 98 g, 0.57 mol) in Et$_2$O (1 L) containing 0.1 g of p-toluenesulfonic acid (Eastman). The solution was then stirred for 1 h at 5°. Solid K$_2$CO$_3$ (Mallinckrodt, 5 g) was then added to the reaction mixture and the resulting suspension stirred an additional 1 h at RT. The reaction was then filtered and the remaining solid washed with Et$_2$O (1 L). The organic solutions were combined and concentrated rotary evaporation (in a flask washed with 1% NEt$_3$ in H$_2$O). The crude 2-(2-iodoethoxy)tetrahydro-2-H-pyran (100 g, 68.9%) was used without further purification.

36C. Ethyl 2-benzylideneamino-2-methyl-4-((tetrahydro-2H-pyran-2-yl)oxy)butyrate A solution of lithium diisopropylamide was prepared by dropwise addition of n-BuLi (Aldrich 1.6M in hexane, 228 mL, 0.365 mol) to a solution of diisopropylamide (Aldrich, 51.6 g, 0.51 mol) in a mixture of dry THF (700 mL) and dry HMPA (Aldrich, 40 mL) kept at 30°–40°. The solution was then cooled to −70° and a solution of ethyl N-benzylidene-1-alaninate (36A, 74.9 g, 0.365 mol) was added dropwise to the solution allowing the reaction mixture warm to −20° for several min. The resulting red solution was then cooled to −70°. 2-(2-Iodoethoxy)tetrahydro-2-H̲-pyran (36B, 98.1 g 0.383 mol) was then added to the solution at such a rate that the temperature in the reaction mixture did not rise above −65°. The solution was allowed to warm slowly to RT and stirred for 14 h. The volume of the solution was reduced to 300 mL by a stream of dry N$_2$ during the last few hours to facilitate the final workup. The reaction was quenched with satd. NaCl (800 mL) and diluted with Et$_2$O (800 mL). The Et$_2$O was removed and the aqueous layer extracted with hexane (500 mL). The Et$_2$O and hexane layers were combined and dried (Na$_2$SO$_4$). The solution was filtered and the solvent removed to give 124 g of crude red oil. Bulb to bulb distillation (in 1% aq. NEt$_3$ washed glassware) (210° bath temperature/0.3 mm) gave 95 g of ethyl 2-benzylideneamino-2-methyl-4-(tetrahydro-2H̲-pyran-2-yl)oxy)butyrate which was homogeneous by vpc and gave acceptable NMR and mass spectra. It was stored under N$_2$ in the refrigerator and was used without further purification.

36D. 2-Benzylamino-2-methyl-4-((tetrahydro-2H̲-pyran-2-yl)Oxy)butanol

A solution of ethyl 2-benzylideneamino-2-methyl-4-((tetrahydro-2H̲-pyran-2-yl)oxy)butyrate (36C, 100.0 g, 0.3 mol) in THF (100 mL) was added slowly to a suspension of lithium aluminum hydride (Alfa, 22.77 g, 0.6 mol) rapidly stirred in dry THF (1 L) at such a rate to maintain a gentle reflux. After the addition was complete the mixture was refluxed for 4 h. The reaction mixture was cooled and treated successively with $H_2O$ (23 mL), 15N NaOH (23 mL) and $H_2O$ (45 mL). The solid was removed by filtration and washed with THF (200 mL). The organic layers were combined and concentrated by rotary evaporation to give 2-benzylamino-2-methyl-4-((tetrahydro-2H-pyran-2-yl)oxy)butanol (81.1 g, 92.0%) as a thick oil which was used without further purification.

36E. 2-Benzylamino-2-methyl-1,4-butanediol

The crude 2-benzylamino-2-methyl-4-((tetrahydro-2H-pyran-2-yl)oxy)butanol (36D, 80.1 g, 0.273 mol) was dissolved in 3N HCl (128 mL). After 5 min the mixture was washed with $Et_2O$ (200 mL). The aqueous solution was concentrated by rotary evaporation to give a thick oil which was cooled and basified with excess 50% NaOH. The oily amine which formed was extracted with $Et_2O$ ($3 \times 200$ mL). The $Et_2O$ extracts were combined and concentrated to give 63.6 g of a thick oil. Distillation gave 49.8 g (94%) of 2-benzylamino-2-methyl-1,4-butanediol as a pale yellow oil (bp 168°–170°/0.35 mm) (C, H, N)

36F. 2-Amino-2-methyl-1,4-butanediol hydrochloride

2-Benzylamino-2-methyl-1,4-butanediol (36E, 31.08 g, 0.149 mol) was dissolved in 95% EtOH (240 mL) containing conc. HCl (21 mL, 0.25 mol) and 5% Pd/C (10.0 g) and reduced in a Parr apparatus at 40 psi over 37 h at RT. The catalyst was then removed by filtration and the solvent removed by rotary evaporation (bath at 60°) to give 20.91 g of 2-amino-2-methyl-1,4-butanediol hydrochloride (90.2%) as a clear, thick, colorless oil with acceptable NMR and mass spectra. It was used without further purification. This compound has been reported as its acetate salt (G. Cardillo et al., Chem. Commun. 1308, 1982), but no data was given. Attempts to duplicate the latter procedure were unsuccessful.

36G. 2-((9-Anthracenylmethyl)aminio)-2-methyl-1,4-butanediol methanesulfonate To a RB flask was added 2-amino-2-methyl-1,4-butanediol hydrochloride (36F) and an equal amount of $NaOCH_3$ (MCB) and enough $CH_3OH$ to form a solution when warmed. The solvent was then removed by rotary evaporation and after addition of 9-anthracenecarbaldehyde (Aldrich), the reaction run following the reductive amination procedure outlined in 2B to give 2-((9-anthracenylmethyl)amino)-2-methyl-1,4-butanediol methanesulfonate mp 212°–213° (dec), (EtOH/$Et_2O$), (C, H, N, S).

EXAMPLE 37

2-(((10-Chloro-1-anthracenyl)methyl)amino)-2-methyl-1,3-propanediol methanesulfonate.9/20 $H_2O$

37A. 10-Chloroanthracene-1-carboxylic acid

Anthracene-1-carboxylic acid (15B, 24g, 0.108 mol) was treated with N-chlorosuccinimide (Aldrich, 24 g, 0.18 mol) in N-methylpyrrolidinone (Eastman, 600 mL) and heated under $N_2$ at 90° for 1.5 h. The reaction mixture was diluted with $H_2O$ (3.5 L), filtered, dried, and the precipitate recrystallized from EtOAc to afford 16.41 g (59%) of 10-chloroanthracene-1-carboxylic acid mp 275°–277°, (C, H, Cl).

37B. Ethyl 10-chloroanthracene-1-carboxylate

10-Chloroanthracene-1-carboxylic acid (37A, 17.3 g, 0.0674 mol), conc. $H_2SO_4$ (1.0 mL), and abs. EtOH (500 mL) was refluxed for 3 days using 4 Å molecular sieves in a Soxhlet extractor to remove $H_2O$. The solvent was removed and then partitioned between EtOAc and satd. $NaHCO_3$. The solvent was then removed from the organic layer to give 14.86 g (77%) of ethyl 10-chloroanthracene-1-carboxylate, which was used without further purification.

37C. 10-Chloro-1-anthracenemethanol

A solution of ethyl 10-chloroanthracene-1-carboxylate (37B, 14.86 g, 0.052 mol) in THF (300 mL) was treated with $LiBH_4$ (Alfa, 1.14 g, 0.052 mol) and refluxed for 16 h. The reaction mixture was poured into ice water and acidified with conc. HCl to pH=2. The solid was filtered, washed with $H_2O$ (500 mL), air dried and then chromatographed on a plug of $SiO_2$ (500 g) using EtOAc as the eluting solvent. The solvent was removed by rotary evaporation to give a solid, which was crystallized from $CCl_4$ to give 10.3 g (81%) of 10-chloro-1-anthracenemethanol mp 138°–140°, (C, H, Cl).

37D. 10-Chloroanthracene-1-carbaldehyde

10-Chloro-1-anthracenemethanol (37C, 8.8 g, 0.036 mol) was dissolved in $CH_2Cl_2$ (200 ml) and treated with $BaMnO_4$ (Aldrich, 15 g, 0.059 mol) for 3 days and briefly brought to reflux. The reaction mixture was filtered, and the filtrate reduced to dryness. The residue was chromatographed by preparative HPLC using $PhCH_3$ as the eluting solvent to give 6.0 g (69%) of crude 10-chloroanthracene-1-carboxaldehyde, which was used without further purification. An analytical sample was recrystallized from $CH_2Cl_2$/hexane mp 139°–140.5°. (C, H, Cl).

37E. 2-(((10-Chloro-1-anthracenyl)methyl)amino)-2-methyl-1,3-propanediol methanesulfonate.9/20 $H_2O$ Using the reductive amination procedure described in 2B. 10-chloroanthracene-1-carbaldehyde (37D) and 2-amino-2-methyl-1,3-propanediol (Aldrich) gave 2-(((10-chloro-1-anthracenyl)methyl)amino)-2-methyl-1,3-propanediol methanesulfonate.9/20 $H_2O$ mp 230°–231° (dec). (EtOH/$Et_2O$), (C, H, Cl, N, S).

EXAMPLE 38

2-(((4-Chloro-10-(2-hydroxyethoxy)-9-anthracenyl)methyl)amino)-2-methyl-1,3-propanediol

38A. 4-Chloro-10-(2-hydroxyethoxy)-9-anthracenecarbaldehyde

A crude isomeric mixture of 1,10- and 4,10-dichloro-9-anthraldehydes (from 5, 36.8 g, 0.133 mol) in 1,2-ethylene glycol (1 L) and THF (200 mL) was treated with KOtBu (MCB, 12.5 g, 0.11 mol) and heated at 80° for 14 h. The reaction mixture was poured into $H_2O$ (2 L). The precipitate was filtered, washed with $H_2O$ (500 mL), sucked dry, then chromatographed on a plug of $SiO_2$ (500 g) using $CH_2Cl_2$ as the initial eluting solvent to remove starting material and by products. The desired product was then eluted with EtOAc to give, after removal of solvent and recrystallization from EtOAc, 3.0 g (7.5%) of 4-chloro-10-(2-hydroxyethoxy)-9-anthracenecarbaldehyde mp 141°–145°, (C, H, Cl).

38B.
2-(((4-Chloro-10-(2-hydroxyethoxy)-9-anthracenyl)methyl)amino)-2-methyl-1,3-propanediol methanesulfonate 3/10 H$_2$O 1/10 i-PrOH Using the reductive amination procedure outlined in 2B, 4-chloro-10-(2-hydroxyethoxy)-9-anthracenecarbaldehyde (38A) and 2-amino-2-methyl-1,3-propanedol (Aldrich) gave 2-(((4-chloro-10-(2-hydroxyethoxy)-9-anthracenyl)methyl)amino)-2-methyl-1,3-propanediol methanesulfonate.3/10 H$_2$O.1.10 i-PrOH mp 156°–158° (dec), (i-PrOH/Et$_2$O), (C, H, Cl, N, S)

EXAMPLE 39
2-Methyl-2-(4,5,10-trichloro-9-anthracenyl)methyl)-1,3-propanediol

39A. 4,5,10-Trichloro-9-anthracenecarbaldehyde

Using the procedure of V. I. Rogovik et al., *Zh Org. Khim.* 3 1315 (1967), and with the modification that the reaction was worked up after heating for 3 h at 95°, 1,8-dichloroanthraquinone (Aldrich, 22 g. 0.08 mol) yielded an impure solid that was purified by preparative HPLC using PhCH$_3$ as the eluting solvent to give 5.29 g (21%) of 4,5,10-trichloro-9-anthracenecarbaldehyde mp 118°–120°, (PhCH$_3$), (C, H, Cl). Almost no product can be isolated using the heating regimen in the reference procedure.

39B.
2-Methyl-2-((4,5,10-Trichloro-9-anthracenyl)methyl)-1,3-propanediol hydrochloride Using the reductive amination procedure outlined in 1, 4,5,10-trichloroanthrancene-10-carbaldehyde (39A) and 2-amino-2-methyl-1,3-propanediol (Aldrich) gave 2-methyl-2-((4,5,10-trichloro-9-anthracenyl)methyl)-1,3-propanediol hydrochloride mp 254°–255° (dec), (EtOH/Et$_2$O), (C, H, Cl, N).

EXAMPLE 40
2-(((10-Chloro-2,3-dimethyl-9-anthracenyl)methyl)amino)-2-methyl-1,3-propanediol

40A.
10-Chloro-2,3-dimethyl-9-anthracenecarbaldehyde 2,3-Dimethylanthraquinone, prepared by the procedure of C. F. Allen and A. Bell, *Org. Syn. Coll. Vol. III*, 310 (1955), was treated with Fe/POCl$_3$/DMF using the procedure of V. I. Rogovik et al., *Zh. Org. Khim.* 3 1315 (1967) to give 10-chloro-2,3-dimethyl-9-anthracenecarbaldehyde mp 150°–153°, (PhCH$_3$/MeOH), (C, H, Cl).

40B.
2-(((10-Chloro-2,3-dimethyl-9-anthracenyl)methyl)amino)-2-methyl-1,3-propanediol hydrochloride Using the reductive amination procedure outlined in 1, 10-chloro-2,3-dimethyl-9-anthracenecarbaldehyde and 2-methyl-2-amino-1,3-propanediol (Aldrich) gave 2-((10-chloro-2,3-dimethyl-9-anthracenylmethyl-)amino)-2-methyl-1,3-propanediol hydrochloride mp 251°–252° (dec), (CH$_3$OH/Et$_2$O), (C, H, Cl, N).

EXAMPLE 41
2-(((2-tert-Butyl-10-chloro-9-anthracenyl)methyl)amino)-2-methyl-1,3-propanediol

41A. 2-tert-Butyl-10-chloro-9-anthracenecarbaldehyde and

41B. 3-tert-butyl-10-chloro-9-anthracenecarbaldehydes 2-tert-Butylanthraquinone (Chemical Dynamics Corporation, P.O. Box 395, 3001 Hadley Road, South Plainfield, NJ, 07080) was reductively formylated using the procedure of V. I. Rogovik et al., *Zh. Org. Khim.* 3 1315 (1967) to give a mixture (1:1) of 2- and 3-tert-butyl-10-chloro-9-anthracenecarbaldehydes, which were separated by preparative HPLC using the shave/recycle technique to obtain 2-tert-butyl-10-chloro-9-anthracenecarbaldehyde mp 126°–129°, (PhCH$_3$/CH$_3$OH), (C, H, Cl), and 3-tert-butyl-10-chloro-9-anthracenecarbaldehyde mp 143°–147°, (PhCH$_3$/CH$_3$OH), (C, H, Cl).

41C.
2-tert-Butyl-10-chloro-9-anthracenylmethyl)amino)-2-methyl-1,3- propanediol hydrochloride.¼ H$_2$O Using the reductive amination procedure described in 1, 2-tert-butyl-10-chloro-9-anthracenecarbaldehyde (41B) and 2-amino-2-methyl-1,3-propanediol (Aldrich) gave 2-(((2-tert-butyl-10-chloro-9-anthracenyl)methyl)amino)-2-methyl-1,3-propanediol hydrochloride.¼H$_2$O mp 249°–250° (dec), (EtoH/Et$_2$O), (C, H, Cl, N).

EXAMPLE 42
2-(((3-tert-Butyl-10-chloro-9-anthracenyl)methyl)amino)-2-methyl-1,3-propanediol hydrochloride Using the reductive amination procedure outlined in 1, 3-tert-butyl-10-chloro-9-anthracenecarbaldehyde (41A) and 2-methyl-2-amino-1,3-propanediol (Aldrich) gave 2-(((3-tert-butyl-10-chloro-9-anthracenyl)methyl)amino)-2-methyl-1,3-propanedol hydrochloride mp 244°–245° (dec) (i-PrOH/Et$_2$O), (C, H, Cl, N)

EXAMPLE 43
2-Methyl-2-(((2,6,10-trichloro-9-anthracenyl)methyl)amino)-1,3- propanediol

43A. 2,6-Dichloroanthraquinone

Using the procedure of M. Nepras et al., *Collection Czechoslov. Chem. Commun.* 28 2707 (1963), the disodium salt of anthraquinone-2,6-disulfonic acid (Aldrich) was converted to 2,6-dichloroanthraquinone mp 295°–297° (lit. mp 291°, *Coll. Czech. Chem. Commun.* 28 2706 (1963)) (C, H, Cl).

43B. 2,6,10-Trichloro-9-anthracenecarbaldehyde

Using the procedure of V. I. Rogovik et al., *Zh. Org. Khim.* 3 1315 (1967) except that the reaction was worked up after heating for 3.25 h at 95°, 2,6-dichloroanthraquinone (43A, 16.67 g, 0.06 mol.) gave 10.12 g of 2,6,10-trichloro-9-anthracenecarbaldehyde (54%) mp 269°–271°, (PhCH$_3$), (C, H, Cl).

43C.
2-Methyl-2-(((2,6,10-trichloro-9-anthracenyl)methyl)amino)-1,3-propanediol hydrochloride Using the reductive amination procedure outlined in 1, 2,6,10-trichloroanthracene-9-carbaldehyde (43B) and 2-amino-2-methyl-1,3-propanediol (Aldrich) gave 2- methyl-2-(((2,6,10-trichloro-9-anthracenyl)methyl)amino)-1,3-propanediol hydrochloride mp 275°–277° (dec), (EtOH/Et₂O), (C, H, Cl, N).

EXAMPLE 44

2-(((10-Butoxy-9-anthracenyl)methyl)amino)-2-methyl-1,3-propanediol

44A. 10-Butoxy-9-butylanthrone
44B. 9-Butoxyanthracene
44C. 10-Dibutyl-9,10-dihydro-9-anthrone
44D. 10-Butyl-9,10-dihydro-9-anthrone A 2 L 2-neck flask fitted with condenser, stirring bar, addition funnel and N₂ line was charged with anthrone (Aldrich, 100 g, 0.515 mol) and 500 mL of EtOH. To the mixture was added quickly a solution containing KOH (Mallinckrodt (85%) 35 g, 0.53 mol) dissolved in 250 mL of EtOH/H₂O (5:1). The resulting deep red solution was warmed to 60°. BuBr (Fisher, 127.6 g, 0.93 mol) was added dropwise over 1 h to the reaction. The reaction was then stirred at 60° for 16 h. Most of the color disappeared after 3 h, leaving a deep yellow solution with precipitate (KBr). The mixture was cooled and filtered. The solvent was removed. The oily dark material was mixed with PhCH₃ (100 mL) and applied to a plug of SiO₂ (1 kg). Fractions of 250 mL were taken using PhCH₃ (5 L ) as eluting solvent. Appropriate fractions were taken and further purified by preparative HPLC using PhCH₃ as eluting solvent and using normal and shave/recycle techniques. From the reaction the following materials were obtained (after separation and purification) in order of elution on SiO₂ with PhCH₃.

44A. 10-Butoxy-9-butylanthracene mp 31°–35°, 9.9 g (6%), (C, H), Rf=0.83

44B. 9-Butoxyanthracene mp 86°–87°, (CH₃OH), 52.11 g (44%), (C, H), Rf=0.81

44C. 10-Dibutyl-9,10-dihyro-9-anthrone mp 108°–109°, isolated after HPLC as an oil which soloidified, 4.0 g (4%), (C, H), Rf=0.53

44D. 10-Butyl-9,10-dihydro-9-anthrone isolated as an oil after HPLC, 41.2 g (29%), (C, H), Rf=0.45

Anthrone (Rf=0.35) was discarded upon isolation during the separations.

44E. 10-Butoxy-9-anthracenecarbaldehyde

10-Butoxyanthracene was formylated using DMF as both solvent and electrophile by the procedure of E. Campaigne and W. L. Archer, *J. Amer. Chem. Soc.* 75 989 (1953), affording 10-butoxy-9-anthracenecarbaldehyde mp 65°–67°, (pentane), (C, H).

44F. 2-(((10-Butoxy-9-anthracenyl)methyl)amino)-2-methyl-1,3-propanediol hydrochloride Using the reductive amination procedure outlined in 1, 10-butoxy-9-anthracenecarbaldehyde 44E) 2-amino-2-methyl-1,3-propanediol (Aldrich) gave 2-(((10-butoxy-9-anthracenyl)methyl)amino)-2-methyl-1,3-propanediol hydrochloride mp 216°–218° (dec), (EtOH/Et₂O), (C, H, Cl, N).

EXAMPLE 45

2-(((10-Butyl-9-anthracenyl)methyl)amino)-2-methyl-1,3-propanediol

45A. 10-Butyl-9-anthracenecarbaldehyde

10-Butyl-9,10-dihydro-9-anthrone (44D) was reduced by the procedure described by H. O. House et al. *J. Org. Chem.* 38 1167 (1973) to give 9-butylanthracene (lit. mp 49°, A. Sieglitz and R. Marx, *Ber.* 56 1619 (1923)). This material was formylated by the procedure described in 2A (except that CH₂Cl₂ was used as the solvent) to give to 10-butyl-9-anthracenecarbaldehyde mp 79°, (CH₂Cl₂/pentane), (C, H), (lit. mp 80.5°–81°, R. H. Martin, and L. van Hove, *Bull. Soc. Chim. Belg.* 61 504 (1952)).

45B. 2-(((10-Butyl-9-anthracenyl)methyl)amino)-2-methyl-1,3-propanediol hydrochloride Using the reductive amination procedure outlined in 1, 10-butyl-9-anthracenecarbaldehyde (45A) and 2-amino-2-methyl-1,3-propanediol (Aldrich) gave 2-(((10-butyl-9-anthracenyl)methyl)amino)-2-methyl-1,3-propanediol hydrochloride mp 225°–227° (dec), (EtOH/Et₂O), (C, H, Cl, N).

EXAMPLE 46

2-((2-Anthracenylmethyl)amino-2-methyl-1,3-propanediol

46A. (2-Anthracenyl)methanol

To a 2 L 3-neck flask fitted with condenser, thermometer and overhead stirrer was added 2-(hydroxymethyl)anthraquinone (Aldrich, 20 g, 0.084 mol), Zn dust (Mallinckrodt, 50 g, 0.765 mol), CuSO₄.5H₂O (Mallinckrodt, 0.5 g), and 28% NH₄OH (Mallinckrodt, 600 mL). The temperature was increased to 80°, and the initial dark-red color faded (about 3 h). After refluxing for an additional 30 min, the mixture was filtered. The filtrate was treated with conc. HCl until acidic, and the resulting precipitate collected. The zinc solid was extracted with EtOAc until the washings were clear, and the EtOAc removed to give an oil. The oil and the precipitate were added to a mixture of conc. HCl (12 ml) in i-PrOH (1200 mL). This solution was concentrated by rotary evaporation to near dryness and CH₃OH (100 mL) was added to give after filtration and drying 13.48 g (77%) of (2-anthracenyl)methanol mp 218°–221° (lit mp 223°–224°, P. Arjunan and K. D. Berlin, *Org. Prep. and Procedure.*, 13(5), 368 (1981)).

46B. 2-Anthracenecarbaldehyde

2-Anthracenylmethanol (46A, 1.0 g, 0.0048 mol) in CH₂Cl₂ (700 mL) was treated with pyridinium chlorochromate (PCC) (Aldrich, 21.56 g, 0.1 mol) and heated for 4 h. The reaction was cooled and filtered through a plug of SiO₂ (500 g) using CH₂Cl₂ as the eluting solvent. After removal of the solvent the crude material was chromatographed on SiO₂ with PhCH₃ as the eluting solvent to afford 0.5 g (51%) of 2-anthracenecarbaldehyde mp 201°–202.5° (lit mp 202°–203°, P. H. Gore, *J. Chem. Soc.* 1616 (1959)), (C, H).

46C. 2-((2-Anthracenylmethyl)amino-2-methyl-1,3-propanediol hydrochloride.9/20 H₂O Using the reductive amination procedure outlined in 1, 2-anthracenecarbaldehyde (46B) and 2-methyl-2-amino-1,3-propanedol (Aldrich) gave 2-((2-anthracenylmethyl)amino-2-methyl-1,3-propanedol hydrochloride.9/20 H₂O mp 224°–226°, (EtOH, Et₂O), (C, H, Cl, N)

ANTITUMOR SCREENING RESULTS

Methods for evaluating the antitumor activity of these compounds are essentially those used in the Tumor Panel by the Developmental Therapeutics Program, Division of Cancer Treatment, National Cancer Institute, A. Goldin, et. al., *Methods in Cancer Research*, Vol. XVI, p.165, Academic Press (1979). Some modifications, in dose level and schedule have been made to increase the testing efficiency.

EXAMPLE 47

Lymphocytic Leukemia P388/0 Test

CD2-$F_1$ mice, of the same sex, weighing 20±3 g are used for this test. Control and test animals are injected intraperitoneally with a suspension of ~$10^6$ viable P388/0 tumor cells on day 0. In each test, several dose levels which bracket the $LD_{20}$ of the compound are evaluated; each dose level group contains six animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) Groups are calculated. The criterion for activity is T/C×100≧120%. Results of P388/0 testing are summarized in Table I below.

TABLE I

P388/0 SCREENING RESULTS

| Compound of Example No. | Optimal Dose (mg/kg) | T/C × 100% (Excluding 30 Day Survivors) | $LD_{20}^A$ |
|---|---|---|---|
| 2A | 425 | +228 | 556 |
| 1 | 150 | +130 | 150 |
| 3B | 110 | +262 | 120 |
| 3C | 90 | +227 | 70 |
| 4B | 130 | +225 | (300) |
| 4C | 160 | +218 | 130 |
| 5C | 300 | +204 | (300) |
| 6 | 165 | +170 | 180 |
| 7 | 94 | +160 | 140 |
| 8B | 450 | +200 | (450) |
| 10B | 300 | +204 | (450) |
| 11B | 200 | +215 | 200 |
| 12B | 45 | +220 | 55 |
| 13B | 120 | +220 | 120 |
| 14B | 387 | +190 | 387 |
| 16C | 300 | +225 | (300) |
| 15E | 77 | +204 | 7 |
| 17C | 150 | +170 | 150 |
| 19B | 281 | +145 | 625 |
| 20B | 440 | +145 | 440 |
| 21 | 277 | +140 | 440 |
| 22C | 600 | +200 | (400) |
| 23 | 450 | +210 | (300) |
| 24B | 118 | +218 | 96 |
| 25B | 100 | +300 | 67 |
| 26B | 300 | +228 | (300) |
| 18 | 200 | +181 | (675) |
| 30G | 180 | +136 | 180 |
| 32C | 625 | +130 | 625 |
| 37E | 155 | +145 | 140 |
| 27B | 155 | +260 | 180 |
| 28B | 225 | +235 | 225 |
| 35C | 550 | +150 | 450 |
| 36G | 150 | +125 | 120 |
| 29B | 125 | +235 | 100 |
| 40B | 450 | +205 | (300) |
| 41C | 450 | +125 | (300) |
| 44F | 104 | +120 | 120 |

TABLE I-continued

P388/0 SCREENING RESULTS

| Compound of Example No. | Optimal Dose (mg/kg) | T/C × 100% (Excluding 30 Day Survivors) | $LD_{20}^A$ |
|---|---|---|---|
| 45B | 159 | +170 | 212 |

$^A$Values in parentheses are the highest non-toxic dose where the $LD_{20}$ was not determined.

EXAMPLE 48

Lymphocytic Leukemia L1210 Test

The protocol for this test is identical to that for P388/0, except that the number of L1210 cells implanted on day 0 is ~105/mouse. The mouse CD2-F1 strain is used, and the criterion for activity is T/C×100 >125%. Results of L1210 testing are summarized in Table II below.

TABLE II

Screening Results for L1210

| Compound of Example No. | Dose (mg/kg) | T/C × 100% Excluding 30 day Survivors |
|---|---|---|
| 3C | 110 | +194 |
| 4C | 150 | +217 |

EXAMPLE 49

Melanotic Melanoma B16

$B6C_3$-$F_1$ mice of the same sex, weighing 20±3 g, are used for this test. A suspension of B16 cells is prepared from a non-necrotic portion of solid tumor tissue obtained from a passage mouse. One gram of tumor is homogenized in 9 mL ice-cold Earle's salts solution and filtered through 1000 mesh screen to remove debris. 0.5 mL of the resulting brei is injected intraperitoneally into each animal. Dosing is carried out as in the P388/0 and L1210 tests. Days of death are recorded for a 60 day period and T/C ratio calculated as in the P388/0 and L1210 tests. The criterion for activity is T/C×100>125%. The results of B16 testing are summarized below in Table III.

TABLE III

Screening Results for B16 Melanoma

| Compound of Example No. | Dose (mg/kg) | T/C × 100% Excluding 60 day Survivors |
|---|---|---|
| 5C | 300 | +200 |
| 3C | 110 | +143 |
| 4C | 130 | +146 |
| 24B | 70 | +146 |
| 12B | 30 | +216 |
| 13B | 110 | +150 |
| 8B | 250 | +125 |
| 25B | 70 | +200 |
| 40B | 300 | +167 |

EXAMPLE 50

Lewis Lung Carcinoma Test

This tumor arose spontaneously in the lung of a C57B1/6 mouse and is maintained by subcutaneous passage in that strain. The solid tumor is excised aseptically and placed in sterile saline. Pieces of viable tumor tissue are minced finely with scissors and forced through a 200 mesh stainless steel screen to disaggregate the tumor cells into a suspension. $10^6$ Viable cells are injected intravenously into the tail vein of BD-F$_1$ mice of the same sex weighing 20±3 g. In each test, several dose levels which bracket the L$_{20}$ for the compound are evaluated. Ten animals are included in each dose level grup, and twenty animals in the untreated control group. The test compounds are prepared and administered on days 1, 5, and 9 as in the P388/0 protocol. The day of death for each animal is recorded, the median identified for each group and the ratios of median survival time for treated (T)/control (C) groups are calculated. The criterion for activity is T/C×100≧140%. The results of Lewis Lung testing are summarized in Table IV.

TABLE IV

Screening Results for Lewis Lung

| Compound of Example No. | Dose (mg/kg) | T/C × 100% Excluding 60 day Survivors |
|---|---|---|
| 3C | 130 | +145 |
| 4C | 200 | +154 |

EXAMPLE 51

Colon 38 Carcinoma Test

This chemically-induced tumor arose in a C57Bl/6 mouse and is maintained as a solid tumor in that mouse strain. The subcutaneously growing solid tumor is aseptically excised from passage mice and placed in sterile saline. The tumor is trimmed free of visible necrotic and connective tissue, then divided into 2-3 mm cubes. A cube is implanted subcutaneously in the ventral thoracic region with a sterile trochar on day 0. In each test several dose levels which bracket the LD$_{20}$ for the compound are evaluated. Ten animals are included in each dose level group and thirty animals in the untreated control group. The test compounds are prepared either in physiologic saline containing 0.05% Tween 80 or distilled water containing 5% dextrose and are administered intraperitoneally on days 1, 5 and 9 after tumor implant. Doses are on a mg/kg basis according to individual animals' body weights. At day 20, the animals are sacrificed and the longest (L) and shortest (W) dimensions of each tumor measured with vernier calipers. Tumor weight is calculated from the formula $$\frac{L \times (W)^2}{2}.$$

The criterion for activity is T/C×100≦42%. The results of Colon 38 testing are summarized in Table V.

TABLE V

Screening Results for Colon 38

| Compound of Example No. | Dose (mg/kg) | T/C × 100% |
|---|---|---|
| 4C | 150 | 38 |

EXAMPLE 52

M5076 Sarcoma Test

This sarcoma arose as a solid tumor in the ovary of a C57Bl/6 mouse and was subsequently converted to the ascitic form for intraperitoneal use. The protocol for this test is identical with that for P388/0. The B6C3-F$_1$ mouse strain is used and the criterion for activity is T/C×100≧125%. Results of M5076 testing are summarized in Table VI below.

TABLE VI

Screening Results for M5076

| Compound of Example No. | Dose (mg/kg) | T/C × 100% |
|---|---|---|
| 3C | 110 | +132 |

EXAMPLE 53

Herpes simplex 1/vero Test

Antiviral testing against *Herpes simplex* 1/vero was done using plaque inhibition methods as outlined in P. Collins and D. J. Bauer, *Proc. N.Y. Acad. Sci.* 284, 49 (1977) and by plaque reduction methods as outlined in P. Collins and D. J. Bauer, *J. Antimicrobial Chemotherapy* 3, Supplement A, 73 (1977). The column headings labeled Score, Toxicity, and Zone of Inhibition refer to the plaque inhibition screen while the IC$_{50}$ heading to the plaque reduction screen.

TABLE VII

Results of Antiviral Screening Against herpes simplex 1/vero

| Compound of Example No. | Score[A] | Toxicity | Zone of Inhibition[B] | IC$_{50}$[B] |
|---|---|---|---|---|
| 2A | −4 | Y | | 1.60 |
| 1 | −3 | Y | | 3.50 |
| 3B | −4 | Y | | 3.50 |
| 4B | −4 | Y | | 4.5(ST6.3) |
| 6 | −3 | Y | | 23.7(ST25) |
| 7 | −4 | Y | | 6.3(ST) |
| 8B | −4 | Y | | |
| 9 | −4 | Y | | 6.3(T) |
| 10B | −3 | Y | 32(ST20) | |
| 12B | −3 | Y | | 20 |
| 13B | −3 | Y | 40(ST23) | |
| 17C | −4 | Y | | 15.2 |
| 19B | −3 | Y | | 14.4 |
| 20B | −2 | Y | | 40 |
| 21 | −4 | Y | | |
| 24B | −3 | N | | |
| 25B | −3 | N | | 32.7 |
| 26B | −3 | N | | 26.0 |
| 18 | −3 | Y | | 12.0 |
| 31C | −3 | Y | | 38.5 |
| 32C | −2 | Y | 23.2 | |
| 33D | −4 | Y | 35(T25) | |
| 29B | −4 | Y | 32(ST) | |
| 45B | −2 | Y | | |

[A]Score; 0 = no inhibition, −1 = 1-25% inhibition, −2 = 26-50% inhibition −3 = 51-75% inhibition, −4 = 76-100% inhibition.
[B]ST = slight toxicity, T = toxic

EXAMPLE 54

Candida albicans Test

Antifungal testing against *Candida albicans* (CN 1863) was done with slight modifications using a combination of broth and agar dilution assays as outlined in Laboratory Handbook of Medical Mycology, Chapter 6, pages 441-446, M. R. McGinnis, Academic Press, New York, NY, 1980

TABLE VIII

Results of Antifungal Testing Against *Candida albicans*(CN1863)

| Compound of Example No. | MIC (mg/L) |
|---|---|
| 2A | >50 |
| 1 | >50 |

Medium: Wellcotest ® sensitivity test agar plus 7% lysed horse blood.

Antibacterial Screening

Antibacterial test against *Mycoplasma smegmatis* (S3264) and *Streptococcus pyogenes* (CN10) was done with slight modifications using standard agar dilution assays as outlined in Manual of Clinical Microbiology Second Ed., E. H. Lennette, E. H. Spaulding and J. P. Truant Eds., American Society for Microbiology, Washington, DC, 1974.

EXAMPLE 55

TABLE IX

Results of Antibacterial Testing Against *Streptococcus pyogenes* (CN10)

| Compound of Example No. | MIC (mg/L) |
|---|---|
| 11B | ≦10 |
| 13B | 100 |

EXAMPLE 56

*Mycoplasma smegmatis* Test

TABLE X

Results of Antibacterial Screening Against *Mycoplasma smegmatis* (53264)

| Compound of Example No. | MIC (mg/L) |
|---|---|
| 2A | 10 |
| 1 | <5 |
| 11B | ≦10 |
| 13B | ≦10 |

EXAMPLE 57

*Trichomonas vaginalis* Test

Antiprotozoal testing against [*Trichomonas vaginalis* was done using methods outlined by R. M. Michaels in *Advances in Chemotherapy* 3, 39–108 (1968).

TABLE XI

Results of Antiprotozoal Testing Against *Trichomonas vaginalis* (in vitro)

| Compound of Example No. | Dose (mg/L) | Result[A] |
|---|---|---|
| 7 | 40 | −4 |
| 6 | 40 | −4 |

(Stenton or Modified Diamond's medium)
[A]Screen Code 0 = no inhibition, −1 = 1–25% inhibition, −2 = 26–50% inhibition, −3 = 51–75% inhibition, −4 = 76–100% inhibition

EXAMPLE 58

*Nippostrongylus brasiliensis* Test

Anthelmintic testing against *Nippostrongylus brasiliensis* was done using methods outlined in D. C. Jenkins, R. Armitage, and T. S. Carrington, *Zeitschrift für Parasitenkunde* 63, 261–269 (1980)

TABLE XII

Results of Anthelmintic Screening Against *Nippostrongylus brasiliensis* (Immature - free living stages)

| Compound of Example No. | MIC (mg/L) |
|---|---|
| 7 | 50 |
| 1 | ≧50 |
| 2A | ≧50 |

EXAMPLE 59

*Eimeria tenella* Testing

Antiprotozoal testing against *Eimeria tenella* was done by using methods outlined in V. S. Latter and D. Wilson, *Parasitology* 79, 169 (1979).

TABLE XIII

Results of Antiprotozoal Screening Against *Eimeria tenella* (in vitro)

| Compound of Example No. | Dose (mg/L) | Result[A] |
|---|---|---|
| 1 | 1.25 | −4 |

[A]Screen Code 0 = no inhibition, −1 = 1–25% inhibition, −2 = 26–50% inhibition, −3 = 51–75% inhibition, −4 = 76–100% inhibition

EXAMPLE 60

$LD_{50}$ Tests

TABLE XIV $LD_{50}$ Values for Selected Compounds (IP single dose - CD-1 Male Mouse)

| Compound of Example No. | $LD_{50}$ (mg/kg) |
|---|---|
| 3B | 100 |
| 1 | 160 |
| 2A | 250 |
| 25B | 110 |

EXAMPLE 61

Formulation Examples

A. Tablet

Compound of Formula I: 500.0 mg
Pregelatinized Corn Starch: 60.0 mg
Sodium Starch Glycolate: 36.0 mg
Magnesium Stearate: 4.0 mg.

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

B. Tablet

Compound of formula (I): 500.0 mg
Corn Starch: 70.0 mg
Lactose: 83.8 mg
Magnesium Stearate: 4.2 mg
Polyvinylpyrrolidone: 14.0 mg
Stearic Acid: 28.0 mg.

The compound of formula (I) is finely ground and intimately mixed with the powdered excipients, corn starch and lactose. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 700 mg each.

C. Capsules

Compound of formula (I): 500.0 mg
Corn Starch: 50.0 mg
Magnesium Stearate: 3.0 mg.

The finely divided compound of formula (I) is mixed with powdered corn starch and wetted with denatured alcohol to densify the powder. The dried powder is mixed with stearic acid and filled into hard-shell gelatin capsules.

D. Syrup

Compound of formula (I): 250.0 mg
Ethanol: 250.0 mg
Glycerin: 500.0 mg
Sucrose: 3,500.0 mg
Flavoring Agent: q.s.
Coloring Agent: q.s.
Preserving Agent: 0.1%
Purified Water: q.s. to 5.0 mL.

The compound of formula (I) is dissolved in ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is throughly mixed.

E. IV Injection

Compound of formula (I): 5.0 mg
Glycerin: q.s. for isotonicity
Preservative: 0.1%
Hydrochloric Acid or Sodium Hydroxide: as needed for pH adjustment
Water for Injection: q.s. to 1 mL.

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. A pharmaceutical formulation containing a compound of formula (I)

$$ArCH_2R^1 \tag{I}$$

or a monomethyl or monoethyl ether thereof, the compound of formula (I) including its ethers containing no more than 30 carbon atoms in total); ethers, esters thereof; acid addition salts thereof; wherein Ar is an anthracene ring optionally substituted by one or two substituents. The substituents will contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the anthracene ring is optionally substituted by a group $NR^3R^4$ containing not more than 5 carbon atoms wherein $R^3$ and $R^4$ are the same or different and each is a $C_{1-3}$ alkyl group;

$R^1$ contains not more than eight carbon atoms and is a group

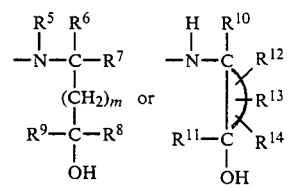

wherein
m is 0 or 1;
$R^5$ is hydrogen;
$R^6$ and $R^7$ are the same or different and each is hydrogen or $C_{1-3}$ alkyl optionally substituted by hydroxy (proving that at least one hydroxy group is present);
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl, except 2-((10-(2-hydroxyethyloxy)-9-anthracenylmethyl)amino-2-methyl-1,3-propanediol with a pharmaceutically acceptable carrier in the form of a tablet, capsule, syrup, or solution.

2. A method of claim 1 for a compound of formula (I) wherein Ar is 9-anthracenyl,

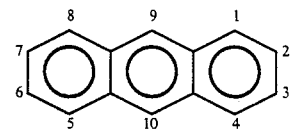

$R^1$ is

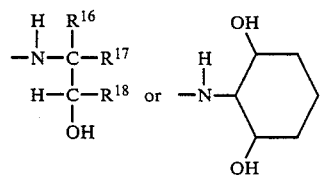

wherein
m is 0;
$R^{16}$ is $CH_2OH$, $CH(CH_3)OH$ or $CH_2CH_2OH$;
$R^{17}$ is hydrogen, $C_{1-3}$ alkyl or $CH_2OH$;
$R^{18}$ is hydrogen or methyl; or a monomethyl or monoethyl ether thereof containing no more than 28 carbon atoms in total; acid addition salts thereof.

3. A method of claim 2 wherein $R^{16}$ is $CH_2OH$ or $CH(CH_3)OH$ and $R^{17}$ is hydrogen, methyl, ethyl or $CH_2OH$; acid addition salts thereof.

4. A method of claim 3 wherein $R^1$ is a diol of the structure

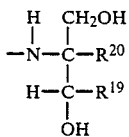

wherein R[19] is hydrogen or methyl and R[20] is hydrogen, methyl or ethyl; acid addition salts thereof.

5. A method of claim 4 wherein R[20] is methyl; acid addition salts thereof.

6. A method of claim 1 wherein the compound of formula (I) is a methane-sulfonic, hydrochloric, ethane-sulfonic, lactic, citric or isethionic acid addition salt.

7. A method of claim 1 wherein a compound of formula (I) is selected from 2-(((10-Chloro-9-anthracenyl)methyl)amino)-2-methyl-1,3-propanediol,
2-((9-Anthracenylmethyl)amino)-2-methyl-1,3-propanediol,
2-Methyl-2-(((10-methylthio-9-anthracenyl)methyl)amino)-1,3-propanediol,
2-(((10-(2-Chloroethyl)-9-anthracenyl)methyl)amino)-2-methyl-1,3-propanediol,
2-(((4,10-Dichloro-9-anthracenyl)methyl)amino)-2-methyl-1,3-propanediol,
2-(((10-Hydroxymethyl-9-anthracenyl)methyl)amino)-2-methyl-1,3-propanediol, 2-Methyl-2-(((10-methyl-9-anthracenyl)methyl)amino)-1,3-propanediol, 2-(((10-Bromo-9-anthracenyl)methyl)amino)-2-methyl-1,3-propanediol,
2-(((10-Chloro-9-anthracenyl)methyl)amino)-2-ethyl-1,3-propanediol,
2-(((4,5-Dichloro-9-anthracenyl)methyl)amino)-2-methyl-1,3-propanediol,
2-(((4-Chloro-9-anthracenyl)methyl)amino)-2-methyl-1,3-propanediol,
2-Methyl-2-(((10-methylsulfinyl-9-anthracenyl)methyl)amino)-1,3-propanediol,
2-(((10-Methoxy-9-anthracenyl)methyl)amino)-2-methyl-1,3-propanediol,
10-((1,1-Bis(hydroxymethyl)ethylamino)methyl)-9-anthracenecarbonitrile,
2-(((10-Bromo-1-anthracenyl)methyl)amino)-2-methyl-1,3-propanediol,
2-((1-Anthracenylmethyl)amino)-2-methyl-1,3-propanediol,
2-(((2-Chloro-9-anthracenyl)methyl)amino)-2-methyl-1,3-propanediol,
2-(((10-Ethylthio-9-anthracenyl)methyl)amino)-2-methyl-1,3-propanediol,
2-(((10-(2-Hydroxyethylthio)-9-anthracenyl)methyl)amino)-2-methyl-1,3-propanediol,
2-(((10-Chloro-9-anthracenyl)methyl)amino)-2-hydroxymethyl-1,3-propanediol,
2-(((3,10-Dichloro-9-anthracenyl)methyl)amino)-2-methyl-1,3-propanediol,
2-(((2,10-Dichloro-9-anthracenyl)methyl)amino)-2-methyl-1,3-propanediol,
2-(((10-Ethoxy-9-anthracenyl)methyl)amino)-2-methyl-1,3-propanediol,
2-Methyl-2-(((10-methylsulfonyl-9-anthracenyl)methyl)amino)-1,3-propanediol,
2-(((3-Chloro-9-anthracenyl)methyl)amino)-2-methyl-1,3-propanediol,
2-(((2-Ethyl-9-anthracenyl)methyl)amino)-2-methyl-1,3-propanediol and 2-(((3-Ethyl-9-anthracenyl)methyl)amino)-2-methyl-1,3-propanediol,
(+−)(2R*,3S*)-2-((9-Anthracenylmethyl)amino)-2-methyl-1,3-butanediol,
2-((9-Anthracenylmethyl)amino)-2-ethoxymethyl-1,3-propanediol,
2-(((10-Chloro-1-anthracenyl)methyl)amino)-2-methyl-1,3-propanediol,
2-(((10-(2-Methoxyethoxy)-9-anthracenyl)methyl)amino)-2-methyl-1,3-propanediol,
2-Methyl-2-(((10-N-morpholino-9-anthracenyl)methyl)amino)-1,3-propanediol,
2-((9-Anthracenylmethyl)amino)-3-methoxy-2-methyl-1-propanol,
2-((9-Anthracenylmethyl)amino)-2-isopropyl-1,3-propanediol,
2-((9-Anthracenylmethyl)amino)-2-methyl-1,4-butanediol,
2-(((10-(1H-Imidazol-1-yl)-9-anthracenyl)methyl)amino)-2-methyl-1,3-propanediol,
(1α,2β,3α)-2-((9-Anthracenylmethyl)amino)-1,3-cyclohexanediol,
2-(((4-Chloro-10-(2-hydroxyethoxy)-9-anthracenyl)methyl)amino)-2-methyl-1,3-propanediol,
2-Methyl-2-(((4,5,10-trichloro-9-anthracenyl)methyl)amino)-1,3-propanediol,
2-(((10-Chloro-2,3-dimethyl-9-anthracenyl)methyl)amino)-2-methyl-1,3-propanediol,
2-(((2-tert-Butyl-10-chloro-9-anthracenyl)methyl)amino)-2-methyl-1,3-propanediol,
2-(((3-tert-Butyl-10-chloro-9-anthracenyl)methyl)amino)-2-methyl-1,3-propanediol,
2-((2-Anthracenylmethyl)amino)-2-methyl-1,3-propanediol,
2-Methyl-2-((2,6,10-trichloro-9-anthracenyl)methyl)amino)1,3-propanediol,
2-(((10-Butoxy-9-anthracenyl)methyl)amino)-2-methyl-1,3-propanediol and
2-(((10-Butyl-9-anthracenyl)methyl)amino)-2-methyl-1,3-propanediol; acid addition salts thereof.

8. A method of claim 7 wherein the compound of formula (I) is a methane-sulfonic, hydrochloric, ethane-sulfonic, lactic, citric or isethionic acid addition salt.

9. A pharmaceutical formulation of claim 1 in the form of a solution for injection.

10. A pharmaceutical formulation of claim 2 in the form of a solution for injection.

11. The method of reducing the cells of a susceptible tumor which comprises contacting said susceptible tumor cells with a tumor reducing amount of the compound or salt of the formulation of claim 1.

* * * * *